(12) United States Patent
Kodama et al.

(10) Patent No.: US 7,595,276 B2
(45) Date of Patent: Sep. 29, 2009

(54) CATALYTIC COMPOSITION FOR OXYCHLORINATION

(75) Inventors: Takashi Kodama, Kitakyushu (JP); Tsuguo Koyanagi, Kitakyushu (JP)

(73) Assignee: JGC Catalysts and Chemicals Ltd., Kawasaki-shi, Kanagawa (JP)

( * ) Notice: Subject to any disclaimer, the term of this patent is extended or adjusted under 35 U.S.C. 154(b) by 0 days.

(21) Appl. No.: 12/219,823

(22) Filed: Jul. 29, 2008

(65) Prior Publication Data

US 2009/0036299 A1    Feb. 5, 2009

(30) Foreign Application Priority Data

Jul. 30, 2007   (JP)   ............... 2007-197825
Nov. 27, 2007   (JP)   ............... 2007-305224

(51) Int. Cl.
*B01J 21/00* (2006.01)
*C07C 17/15* (2006.01)
*B01J 23/00* (2006.01)
*B01J 20/00* (2006.01)
*B01J 21/04* (2006.01)
*B01J 23/02* (2006.01)

(52) U.S. Cl. ............... 502/244; 502/263; 502/346; 502/355; 502/407; 502/439

(58) Field of Classification Search ............... 502/244, 502/231, 263, 346, 355, 407, 439; C07C 17/15; B01J 27/138
See application file for complete search history.

(56) References Cited

U.S. PATENT DOCUMENTS

| | | | | |
|---|---|---|---|---|
| 1,966,362 A | * | 7/1934 | Stockton | ............... 502/411 |
| 6,613,710 B2 | * | 9/2003 | Ray et al. | ............... 502/68 |
| 2007/0004583 A1 | * | 1/2007 | Cooker et al. | ............... 502/60 |
| 2007/0112235 A1 | * | 5/2007 | Kramer et al. | ............... 570/243 |

FOREIGN PATENT DOCUMENTS

| | | |
|---|---|---|
| JP | S45-39616 | 12/1970 |
| JP | H11-090232 | 4/1999 |
| JP | H11-090233 | 4/1999 |
| JP | H11-090234 | 4/1999 |
| JP | 2005-000730 | 1/2005 |
| JP | 2005-000731 | 1/2005 |
| JP | 2007-144247 | * 6/2007 |

\* cited by examiner

*Primary Examiner*—Roy King
*Assistant Examiner*—Alexander Polyansky
(74) *Attorney, Agent, or Firm*—Manabu Kanesaka

(57) ABSTRACT

The present invention provides a catalytic composition for oxychlorination excellent in the fluidity, the capability of suppressing lowering of the fluidity, and the attrition resistance as well as in the selectivity for EDC and the capability of suppressing combustion of ethylene.

The catalytic composition for oxychlorination contains silica alumina particles in the range from 5 to 40 wt % when expressed as an oxide thereof, copper in the range from 5 to 20 wt % when expressed as an oxide thereof (CuO), and alumina as a carrier in the range from 40 to 90 wt % when expressed as that of $Al_2O_3$. The silica alumina particles are prepared by coating silica particles with alumina, and have the average particle diameter in the range from 3 to 100 nm. A content of alumina in the silica alumina particles is in the range from 0.1 to 10 wt %.

9 Claims, No Drawings

CATALYTIC COMPOSITION FOR OXYCHLORINATION

BACKGROUND OF THE INVENTION

1. Technical Field

The present invention relates to a catalytic composition for oxychiorination. More specifically, this invention relates to a catalytic composition for oxychlorination which is excellent in such characteristics as fluidity, the capability of suppressing deterioration in fluidity, and attrition resistance and also is excellent in such characteristics as activity, selectivity for 1,2-dichlorethane (sometimes referred to as EDC hereinafter), and the capability of suppressing combustion of ethylene.

2. Background Technology

For chlorination of aliphatic hydrocarbons by oxychlorination, there has generally been used a catalyst in which a metal salt is carried on a porous carrier such as alumina, silica alumina, and clay. Especially, there has been used in the industrial field, for a long time, a catalyst for a fluidized bed in which cupric chloride is carried on an alumina carrier by impregnation, when the EDC is manufactured by means of oxychlorination of ethylene. In this catalyst, the copper which is an active component moves or sublimes to cause deterioration of the activity or deterioration of the fluidity, and as a result, temperature distribution in the catalyst layer becomes heterogeneous and combustion of ethylene rapidly proceeds in a heated area, which disadvantageously leads to deterioration of the selectivity for EDC or deterioration of the yield. To suppress movement or sublimation of copper, and furthermore to improve the selectivity for EDC, such a material as an alkali metal, an alkali earth metal, or a rare earth metal is added to the catalyst.

On the other hand, there has been known the catalyst obtained by simultaneously precipitating a carrier component and an active component (this method is sometimes referred to as "co-precipitation method" hereinafter) and spray-drying the precipitates (Refer to Patent document 1). Furthermore, there has been known the catalyst prepared by the coprecipitation method and having such a material as an alkali metal, an alkali earth metal, or a rare earth metal on the catalyst (Refer to Patent documents 2 to 4).

The present inventors disclosed that the catalyst, which is prepared by using a pseudo boehmite alumina slurry previously prepared as an alumina source, adding an active component such as copper and an auxiliary catalytic component such as an alkali, an alkali earth metal, or a rare earth metal to the boehmite alumina slurry, and spray-drying the components, little shows lowering of the fluidity and also shows high activity and high selectivity (Refer to Patent documents 5 and 6).

In the fluidized bed oxychlorination method based on the conventional technology, because the activity and selectivity of the catalyst are apt to lower or the catalyst is apt to be scattered as time goes by, new catalyst is added while a portion of old catalyst is being taken away. Furthermore, the activity and the selectivity of the conventional catalysts using alumina as a carrier are relatively high in the initial state, but the performances are not preserved for a long time, and therefore in a case of a catalyst using silica alumina as a carrier, not only the initial activity and selectivity are insufficient, but also combustion of ethylene rapidly proceeds, which leads to deterioration of the selectivity for EDC with the yield lowered.

For the reasons as described above, it is strongly required to suppress combustion of ethylene and also to suppress deterioration of the selectively for EDC and lowering of the yield.

Patent document 1: JP S45-39616 B
Patent document 2: JP H11-90232 A
Patent document 3: JP H11-90233 A
Patent document 4: JP H11-90234 A
Patent document 5: JP 2005-000730 A
Patent document 6: JP 2005-000731 A

DISCLOSURE OF THE INVENTION

The present inventors devoted themselves to investigations to find out that it is possible to suppress combustion of ethylene and also to suppress deterioration in the selectivity for EDC and lowering of yield of the oxychlorination catalyst by blending silica alumina particles, especially silica particles coated with alumina in an alumina carrier, and completed the present invention.

An object of the present invention is to provide a catalytic composition for oxychlorination which is excellent in such properties as fluidity, a capability of suppressing deterioration of the fluidity and attrition resistance and is also excellent in such properties as activity, selectivity for EDC and a capability of suppressing combustion of ethylene. Another object of the present invention is to provide a method of manufacturing the catalytic composition for oxychlorination as described above.

The catalytic composition for oxychlorination according to the present invention comprises silica alumina particles with the content in the range from 5 to 40 wt % as an oxide, copper with the content in the range from 5 to 20 wt % as an oxide (CuO), and alumina as a carrier with the contents from 40 to 90 wt % as converted to that of $Al_2O_3$.

The silica alumina particles are preferably prepared by coating silica particles with alumina.

An average particle diameter of the silica alumina particles is preferably in the range from 3 to 100 nm, and a content of alumina in the silica alumina particles is preferably in the range from 0.1 to 10 wt %.

Furthermore, the catalytic composition preferably contains an alkali earth metal, and a content of the alkali earth metal is preferably in the range from 0.1 to 6 wt % when expressed as that of an oxide thereof (MO: M representing the alkali earth metal element).

Furthermore, the catalytic composition preferably contains a rare earth metal, and a content of the rare earth metal is preferably in the range from 0.1 to 6 wt % when expressed as that of an oxide thereof ($RE_2O_3$: RE represents the rare earth metal element).

Furthermore, the catalytic composition preferably contains an alkali metal, and a content of the alkali metal is preferably in the range from 0.1 to 3 wt % when expressed as that of an oxide thereof ($N_2O$: N representing an alkali metal element).

The alkali earth metal is preferably magnesium.
The alkali metal is preferably potassium.

A method (1) of manufacturing the catalytic composition for oxychlorination according to the present invention comprises the following steps (a) to (c):

(a) a step of preparing a slurry for spray drying by adding a dispersion liquid of silica alumina particles, an acid, and an aqueous solution of cupric nitrate in a pseudo boehmite alumina slurry;

(b) a step of spray drying the slurry; and (c) a step of calcining the microparticles obtained in step (b).

pH of the slurry for spray drying is preferably in the range from 1.5 to 5.5.

The silica alumina particles are preferably prepared by coating silica particles with alumina.

An average particle diameter of the silica alumina particles is preferably in the range from 3 to 100 nm, and a content of alumina in the silica alumina particles is preferably in the range from 0.1 to 10 wt %.

In step (a) above, furthermore an aqueous solution of an alkali earth metal salt is preferably added.

In step (a) above, furthermore an aqueous solution of a rare earth metal salt is preferably added.

In step (a), furthermore an aqueous solution of an alkali metal salt is preferably added.

A method (2) of manufacturing a catalytic composition for oxychlorination according to the present invention comprises the following steps (a) to (f):

(a) a step of mixing an aqueous solution of an alkali metal aluminate, a dispersion liquid of silica alumina particles, and an aqueous solution of cupric salt in an aqueous solution of an aluminum salt;

(b) a step of preparing a slurry for spray drying by cleaning the mixture slurry;

(c) a step of spray drying the slurry;

(d) a step of cleaning the spray dried slurry;

(e) a step of drying the slurry; and (f) a step of calcining the slurry.

pH of the slurry for spray drying is preferably in the range from 4 to 9.5.

The silica alumina particles are preferably prepared by coating silica particles with alumina.

An average particle diameter of the silica alumina particles is preferably in the range from 3 to 100 nm, and a content of alumina in the silica alumina particles is preferably in the range from 0.1 to 10 wt %.

In step (a) above, it is preferably to mix, in step (a) above, at least one of an aqueous solution of a metal salt selected from the group consisting of an aqueous solution of an alkali earth metal salt, an aqueous solution of a rare earth metal salt, and an aqueous solution of an alkali metal salt in the aqueous solution of an aluminum salt.

In step (a) above, it is preferably to mix, in step (a) above, at least one of an aqueous solution of a metal salt selected from the group consisting of an aqueous solution of an alkali earth metal salt, an aqueous solution of a rare earth metal salt, and an aqueous solution of an alkali metal salt together with or in succession to the aqueous solution of cupric salt.

The catalytic composition for oxychlorination according to the present invention contains, by a prespecified content, silica alumina particles, especially silica particles coated with alumina. Because of the characteristic, although a specific surface area of the catalyst is rather low, the catalyst is excellent in heat resistance and hydrothermal resistance and is also excellent in fluidity and the capability in suppressing lowering of the fluidity, and attrition resistance, and can show high activity, selectivity, and capability of suppressing combustion of ethylene for a long time.

A method (3) of manufacturing a catalytic composition for oxychlorination according to the present invention provides a catalytic composition for oxychlorination containing alumina and copper with the copper content in the range from 5 to 20 wt % when expressed as that of CuO and also with the halogen content of 5 wt % or below, and the method comprises the following steps (a) to (d):

(a) a step of adding carboxylic acid and/or hydroxycarboxylic acid in a pseudo boehmite alumina slurry and aging the mixture;

(b) a step of furthermore adding an acid and an aqueous solution of cupric nitrate in the mixture to prepare a slurry for spray drying;

(c) a step of spray drying the slurry; and (d) a step of calcining the microparticles obtained in step (c).

The carboxylic acid and/or the hydroxycarboxylic acid are preferably one or more selected from the group consisting of formic acid, acetic acid, oxalic acid, acrylic acid (unsaturated carboxylic acid), gluconic acid, malic acid, malonic acid, succinic acid. glutaric acid, adipic acid, sebacic acid, maleic acid, fumaric acid, phthalic acid, α-lactic acid, β-lactic acid, γ-hydroxy valeric acid, glyceric acid, tartaric acid, citric acid, tropic acid, and benzilic acid.

In step (a) above, a molar ratio between a number of moles of the carboxylic acid and/or hydroxycarboxylic acid ($M_C$) and a number of moles of $Al_2O_3$ in the pseudo boehmite alumina slurry ($M_A$) ($M_C/M_A$) is preferably in the range from 0.005 to 0.1.

pH of the slurry for spray drying is preferably in the range from 3 to 5.

In step (b) above, preferably an aqueous solution of an alkali earth metal salt is added to obtain a catalytic composition for oxychlorination with a content of the alkali earth metal in the range from 0.1 to 6 wt % when expressed as that of an oxide thereof (MO: M representing the alkali earth metal element).

The alkali earth metal is preferably magnesium.

In step (b) above, preferably an aqueous solution of a rare earth metal is added to obtain a catalytic composition for oxychlorination with a content of the rare earth metal in the range from 0.1 to 6 wt % when expressed as that of an oxide thereon ($RE_2O_3$: RE representing the rare earth metal element).

In step (b) above, it is preferably to obtain a catalytic composition for oxychlorination with the alkali metal content in the range from 0.1 to 3 wt % when expressed as that of an oxide thereof ($N_2O$: N representing an alkali element)

The alkali metal is preferably potassium.

With the method (3) of manufacturing a catalytic composition for oxychlorination according to the present invention, it is possible to reduce corrosion of a catalyst manufacturing apparatus and scattering of a halogen gas or the like into the atmospheric air and also to manufacture a catalytic composition for oxychlorination with a small content of halogen which is excellent in the activity, the selectivity for EDC, and the capability of suppressing combustion of ethylene as well as in such characteristics as the capability of preserving the long-term stability and the attrition resistance.

BEST MODE FOR CARRYING OUT THE INVENTION

[Catalytic Composition for Oxychlorination]

A catalytic composition for oxychlorination according to the present invention contains silica alumina particles, copper, and alumina as a carrier.

A content of copper is preferably in the range from 5 to 20 wt % and more preferably in the range from 8 to 15 wt % when expressed as that of an oxide thereof (CuO). When the copper content is less than 5 wt %, the activity is insufficient, and a yield of EDC drops. When the copper content is over 20 wt %, combustion of ethylene as a feed proceeds rapidly with the EDC yield dropped, and a quantity of copper is excessive so that a portion of the copper moves to external surfaces of the catalyst particles or is sublimated to cause lowering of the fluidity.

The silica alumina particles constituting the catalytic composition according to the present invention may be general silica alumina composite oxide particles comprising silica and alumina, but are preferably prepared by coating silica particles with alumina.

The present applicant already found out that the catalytic composition using alumina as a carrier and containing a small quantity of silica particles has improved heat resistance and hydrothermal resistance, and filed a patent application (Refer to Japanese Patent Application No. 2006-192959). However, the capability of suppressing combustion of ethylene is not sufficient, and also the selectivity for EDC and the yield are still to be improved.

When the silica alumina particles are those prepared by coating silica particles with alumina, heat resistance and hydrothermal resistance of a catalyst are improved, and in addition combustion of ethylene can be suppressed, and therefore it is possible to obtain a catalyst excellent in such properties as the selectivity for EDC and the yield.

The reason why the improved properties as described above are obtained has not been fully clarified, but it is conceivable that, when silica particles are blended in the alumina carrier, the silica particles react to alumina as a carrier to show the so-called solid acidity and the solid acid contributes to the oxidizing reaction (combustion of ethylene), and also that, when the silica particles are coated with alumina, because inside of the silica alumina particles comprises silica particles and the surface is not different from alumina, the heat resistance and hydrothermal resistance are improved like in silica particles while suppressing combustion of ethylene.

A content of alumina in the silica alumina particles is preferably in the range from 0.1 to 10 wt %, more preferably in the range from 0.2 to 5 wt %, and still more preferably in the range from 0.5 to 3 wt %.

When the content of alumina in the silica alumina particles is less than 0.1 wt %, the silica particles are not fully coated with alumina, and in this case the silica alumina particles can not provide the properties like those of alumina, and therefore the heat resistance and the hydrothermal resistance of the catalyst prepared by using the silica alumina particles are not sufficient.

When the content of alumina in the silica alumina particles is over 10 wt %, fluidity of the catalytic composition may become lower and also the attrition resistance may be insufficient.

An average particle diameter of the silica alumina particles is preferably in the range from 3 to 100 nm, and more preferably in the range from 5 to 50 nm.

When the average particle diameter of the silica alumina particles is less than 3 nm, it is possible to completely coat the silica particles with alumina, and silica easily bonds to alumina which is a main component of the carrier to form silica alumina, and as a result combustion of ethylene proceeds with the selectivity for EDC and the yield deteriorated.

When the average particle diameter of the silica alumina particles is over 100 nm, the reactivity with active components such as copper as well as with alkali metals, alkali earth metals, and the selectivity for EDC may be deteriorated, and furthermore the attrition resistance may become lower with the effect of improving heat resistance and hydrothermal resistance lost.

A content of the silica alumina particles as described above in a catalyst is preferably in the range from 5 to 40 wt %, and more preferably in the range from 10 to 25 wt % when expressed by that of an oxide thereof.

When the content of silica alumina particles in the catalyst is less than 5 wt %, the heat resistance and the hydrothermal resistance are not sufficiently improved, and sometimes the high activity and the selectivity in the initial stage can not be preserved for a long time.

When the content of the silica alumina particles in the catalyst is over 40 wt % as that of an oxide thereof, sometimes the attrition resistance may become lower with the sufficient effect for improving the heat resistance and the hydrothermal resistance lost.

There is no specific restriction over the silica alumina particles used in the present invention so long as the silica alumina particles as described above can be obtained, and the silica alumina particles can be obtained, for instance, by adding an aluminum compound, a partially hydrolyzed product of an aluminum compound, a hydrolyte of an aluminum compound, an alumina sol or the like in a silica sol so that a content of alumina in the obtained silica alumina particles would be in the range described above, and by adjusting the pH and aging the product according to the necessity.

Any known silica sol may be used in the present invention, and a average particle diameter of the silica sol is preferably in the range from about 3 to about 100 nm. When the average particle diameter of the silica sol is in the range described above, an average particle diameter of the obtained silica alumina particles is in the range described above, and the silica sol can advantageously be used.

The aluminum compound used in the present invention is, for instance, an inorganic aluminum salt such as aluminum chloride, aluminum nitride, aluminum sulfate, aluminum acetate, or an organic aluminum salt.

Especially, a cationic hydrated metal compound, which is a partially hydrolyzed product of the metal salt expressed by the following chemical formula can advantageously be used:

$$[M_2(OH)_n X_{(2a-n)/b}]_m \quad [1]$$

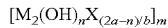

(wherein M represents a metal cation having trivalence or more, X represents an anion, a represents a valence of the metal cation, and b represents a valence of the anion. $1<n<5$, $n<2a$, and $1 \leq m$)

When the cationic hydrated metal compound is used, a surface of the silica colloid is coated with alumina and at the same time positively charged, and the particles are highly dispersed in the alumina carrier, which is conceivably the reason for the desirable effects provided by the silica alumina particles according to the present invention.

The catalytic composition for oxychlorination according to the present invention preferably contains an alkali earth metal, and a content of the alkali earth metal is preferably in the range from 0.1 to 6 wt %, and more preferably in the range from 0.2 to 4 wt % when expressed as that of an oxide thereof (MO: M representing the alkali earth metal element). When the content of the alkali earth metal is less than 0.1 wt %, the bulk density and attrition resistance of the catalyst obtained by using the composition are apt to become lower. When the content of the alkali earth metal is over 6 wt %, sometimes a pore volume of a catalyst obtained by using the composition is low and the activity is insufficient.

The alkali earth metal is preferably magnesium, and when magnesium is used, a catalyst excellent in the attrition resistance can be obtained without lowering the activity.

Furthermore, the catalyst according to the present invention may contain an alkali metal, and a content of the alkali metal is preferably in the range from 0.1 to 3 wt % and more preferably in the range from 0.2 to 2 wt % when expressed as that of an oxide thereof ($N_2O$: N representing the alkali metal element). When the content of the alkali metal is less than 0.1 wt %, the effect of suppressing combustion of ethylene is not sufficient, and a yield of EDC becomes lower. When the content of the alkali metal is over 3 wt %, the reactivity of Cl becomes lower with the EDC yield lowered.

The alkali metal is preferably potassium. When potassium is used, the effect of suppressing oxidation of ethylene is more mild as compared to the effect provided by other alkali metals, and oxidization of ethylene can easily be suppressed without substantially lowering the activity of giving chloride generated via oxygen from a hydrochloride acid to ethylene which is a main reaction, and oxidization of ethylene can easily be suppressed.

Furthermore, the catalyst according to the present invention may contain a rare earth metal, and a content of the rare earth metal is preferably in the range from 0.1 to 6 wt % and more preferably in the range from 0.2 to 4 wt % when expressed as that of an oxide thereof ($RE_2O_3$: RE representing the rare earth metal element). When the content of the rare earth metal is less than 0.1 wt %, the selectivity for EDC becomes lower, and the effect of suppressing combustion of ethylene is insufficient, so that also the EDC yield becomes lower. When the content of the rare earth metal is over 6 wt %, the reactivity of Cl becomes lower with the EDC yield dropped.

The catalytic composition according to the present invention preferably contains, excluding alumina in the silica alumina particles, alumina as a carrier in the range from 40 to 90 wt % and more preferably in 60 to 82 wt % when expressed as that of $Al_2O_3$. When the alumina content is less than 40 wt %, a specific surface area and a pore volume of the catalyst become smaller, and in addition contents of active components become higher, so that sometimes the activity of the catalyst can not be shown effectively. Also the attrition resistance may be insufficient. When the alumina content is over 90 wt %, quantities of silica alumina particles, active components and/or promoters such as a rare earth metal, an alkali earth metal, and an alkali metal decrease, and sometimes the activity or the selectivity may be insufficient.

When the carrier alumina is $\gamma$-$Al_2O_3$, a specific surface and a pore volume of the catalyst are large, and in this case both the activity and the selectivity of the catalyst are excellent.

In the catalytic composition for oxychlorination according to the present invention, the average particle diameter is preferably in the range from 40 to 75 μm and more preferably in the range from 45 to 70 μm. When the average particle diameter is less than 40 μm, sometimes the sufficient fluidity can not be obtained, and the catalyst loss may increase. When the average particle diameter is over 75 μm, the sufficient fluidity may not be obtained like in the case when the average particle diameter is small.

As for the particle diameter distribution, it is preferable that the particle diameters are substantially homogeneous, and a percentage of microparticles with the particle diameter of less than 30 μm is preferably 10 wt % or less, and a percentage of particles with the particle of more than 90 μm is preferably not more than 20 wt %. The particles may further be clarified minutely according to the necessity.

The particle diameter distribution can be measured by the micromesh sieve method.

A specific surface area of the catalytic composition is preferably in the range from 150 to 350 $m^2/g$, and more preferably in the range from 200 to 300 $m^2/g$. When the specific surface area is less than 150 $m^2/g$, the efficiency of the reaction for adding Cl to ethylene becomes lower, and also a yield of EDC as a target product becomes lower. When the specific surface area of the catalytic composition is over 350 $m^2/g$, the oxidizing reaction of ethylene may become more active.

A pore volume of the catalytic composition is preferably in the range from 0.25 to 0.40 ml/g, and more preferably in the range from 0.30 to 0.35 ml/g. When the pore volume is less than 0.25 ml/g, also a specific surface area of the catalytic composition is small, and sometimes the EDC yield may be insufficient. In addition, sometimes the close bulk density of the catalytic composition becomes higher, which may in turn deteriorate the fluidity during the reaction. When the pore volume is over 0.40 ml/g, the attrition resistance is insufficient, and a quantity of the catalyst scattered during the reaction is apt to becomes larger.

The close bulk density (CBD) of the catalytic composition is preferably in the range from 0.85 to 1.20 g/ml, and more preferably in the range from 0.95 to 1.10 g/ml. When the close bulk density (CBD) is less than 0.90 g/ml, the catalyst is too light and may be scattered to outside of a reaction vessel. When the close bulk density (CBD) is over 1.20 g/ml, sometimes flow instability may occur, and in that case, sometimes combustion of ethylene caused by polarized flow or polarized heat may cause disadvantageous problems.

The close bulk density (CBD) can be obtained by filling a prespecified quantity of a catalyst having been subjected to a heating process under prespecified conditions in a quantitative vessel (such as a measuring cylinder), fully vibrating the catalyst to condense the catalyst particles as much as possible, measuring the volume in the state, and dividing a quantity of filled catalyst by the volume.

[Method of Manufacturing a Catalytic Composition for Oxychlorination (1)]

A method (1) of manufacturing a catalytic composition for oxychlorination according to the present invention comprises the following steps (a) to (c):

(a) a step of preparing a slurry for spray drying by adding a dispersion liquid of silica alumina particles, an acid, and an aqueous solution of cupric nitrate in a pseudo boehmite alumina slurry;

(b) a step of spray drying the slurry; and (c) a step of calcining the microparticles obtained in step (b).

Step (a)

Pseudo boehmite alumina is used as an alumina source in the present invention. The pseudo boehmite alumina ($Al_2O_3 \cdot nH_2O$, n: 0.5 to 2.5) is a crystalline alumina hydrate, and generally comprises fibrous secondary particles based on bundles fibrous primary particles.

The primary particles of the pseudo boehmite alumina used in the present invention preferably have the average length ($L_1$) in the range from 1 to 10 nm and the average width ($W_1$) in the range from 0.5 to 3 nm.

When the average length ($L_1$) of the primary particles is less than 1 nm, the primary particles react with silica alumina particles described below to form a composite oxide, and not only the effect of improving the heat resistance and hydrothermal resistance can not be obtained, but also the activity and the selectivity in the initial stage are insufficient, and in addition combustion of ethylene proceeds, and the selectivity for EDC and the yield are apt to become lower.

When the average length ($L_1$) of the primary particles is over 10 nm, sometimes the close bulk density of the obtained catalytic composition drops and the attrition resistance is insufficient.

When the average width ($W_1$) of the primary particles is less than 0.5 nm, alumina silica composite oxide is formed, and not only the effect of improving the heat resistance and hydrothermal resistance can not be obtained, but also the activity and the selectivity in the initial stage are insufficient, and in addition combustion of ethylene proceeds, and the selectivity for EDC and the yield are apt to become lower.

When the average width ($W_1$) is over 3 nm, sometimes the close bulk density of the obtained catalytic composition drops and the attrition resistance is insufficient.

A size of the primary particles can be obtained by photographing the primary particles with a scan electron microscope.

Any known pseudo boehmite alumina may be used in the present invention so long as the requirement for a size thereof is satisfied.

The pseudo boehmite alumina can be obtained, for instance, by reacting an aqueous solution of an alkaline aluminum salt to an acidic substance and cleaning or aging the reaction product according to the necessity. Furthermore, the pseudo boehmite alumina can be obtained also by mixing an aqueous solution of sodium aluminate with a required concentration and an aqueous solution of aluminum sulfate for reaction, and the aging the reaction product, if required.

A concentration of the pseudo boehmite alumina slurry used in the present invention is preferably in the range from 2 to 20 wt % and more preferably in the range from 5 to 18 wt % when expressed as that of $Al_2O_3$. When the concentration is less than 2 wt %, the concentration of the slurry for spray drying drops. In that case, a percentage of excessively small particles becomes high, and because the catalyst can not be captured by a cyclone, and a loss of the catalyst increases. When the concentration is over 20 wt %, sometimes a concentration of the slurry for spray drying is too high and also the viscosity is too high, which makes it difficult to spray-dry the slurry. Even if the slurry can be spray-dried, dispersibility of active components is insufficient and the performance of the obtained catalyst is insufficient, or such properties as the attrition resistance or close bulk density (CBD) become lower.

In this step, an acid is added to the pseudo boehmite alumina slurry. As the acid, any mineral acid such as hydrochloric acid, nitric acid, and sulfuric acid or any organic acid such as an acetic acid may be used. Especially nitric acid is preferable, because the aggregated particles of the pseudo boehmite slurry (secondary particles) can be homogenized and a catalytic composition with excellent attrition resistance or high close bulk density (CBD) can be obtained. At the same time, it is possible to obtain a catalytic composition which does not decay a manufacturing device when manufacturing a catalyst and containing halogens little.

A quantity of the acid to be added is preferably in the range from 0.001 to 0.1 moles and more preferably in the range from 0.005 to 0.05 moles per 1 mole of $Al_2O_3$ in the slurry. When the quantity of the acid is less than 0.001 moles, the aggregated particles (secondary particles) of the pseudo boehmite alumina slurry remain heterogeneous, and sometimes such performances as attrition resistance or close bulk density (CBD) of the obtained catalytic composition may drop. Furthermore, pH of the pseudo boehmite slurry may be over 6. In that case, copper components added later or most of an alkali earth metal or rare earth metal components are deposited before being spray-dried, so that the components can not be deposited in the homogeneously dispersed state on the alumina carrier. In this case, the effect for suppressing oxidization of ethylene is lost with such properties as the long-term fluidity deteriorated. When the quantity is over 0.1 mole, most of the pseudo boehmite alumina reacts to the acid to be dissolved in the acid. In this case, a specific surface area or a pore volume of the obtained catalytic composition becomes slammer and the activity is insufficient.

The acid used in the present invention generally has the concentration in the range from 10 to 35 wt %.

pH of the pseudo boehmite slurry is preferably in the range from 2 to 6, and more preferably in the range from 3 to 5.

Then a dispersion liquid of silica alumina particles is added.

The silica alumina particles as described above are used in this step.

A quantity of used silica alumina particles is adjusted so that a content of the silica alumina particles in the obtained catalytic composition is in the range from 5 to 40 wt % and more preferably in the range from 10 to 25 wt %.

There is no specific restriction over a concentration of a dispersion liquid of the silica alumina particles, and the concentration is generally in the range from 5 to 30 wt % when expressed by that of an oxide thereof.

Then an aqueous solution of cupric nitrate is added.

A quantity of the aqueous solution of cupric nitrate is adjusted so that a content of copper in the finally obtained catalytic composition in the range from 5 to 20 wt % and preferably is in the range from 10 to 15 wt % when expressed as that of an oxide thereof (CuO).

In step (a), preferably at least one of an aqueous solution of an alkali earth metal salt, an aqueous solution of a rare earth metal salt, and an aqueous solution of an alkali metal salt is preferably added so that a content of each of the oxides in the finally obtained catalytic composition would be in the range described above. These aqueous solutions are preferably together with or after addition of the aqueous solution of a cupric nitrate.

As the alkali earth metal salt, a nitrate, a hydrochloride, or a hydrosulfate of magnesium, calcium, barium or the like can be used, and especially when a nitrate is used, a degree of corrosion of a catalyst manufacturing device can be reduced, and also it is possible to obtain a catalyst containing halogens only a little and also producing a organic halogenated compounds as byproducts only a little.

Especially when magnesium nitrate is used, it is possible to obtain a catalytic composition with the activity deteriorated little which can suppress generation of organic halogenated compounds as byproducts and is excellent in the attrition resistance.

As the rare earth metal salt, a nitrate, a hydrochloride, or a hydrosulfate of lanthanum, cerium, or the like may be used. Especially, when the nitrate is used, a degree of corrosion of a catalyst manufacturing device can be reduced, and it is possible to obtain a catalytic composition which contains halogens only a little, is excellent in the selectivity for EDC and also capable of suppressing combustion of ethylene, and produces organic halogenated compounds as byproducts only a little.

As the alkali metal salt, a nitrate, a hydrochloride, or a hydrosulfate of sodium, potassium, or the like can be used, and the nitrate is especially preferable. When potassium nitrate is used, it is possible to obtain a catalytic composition which contains halogens only a little, is excellent in the selectivity for EDC, can suppress combustion of ethylene, and produces organic halogenated compounds as byproducts only a little.

There is no specific restriction over a concentration of the aqueous solution, but generally the concentration is in the range from 1 to 30 wt %. Furthermore, there is not specific restriction in a sequence of adding the aqueous solutions, and the aqueous solutions other than the aqueous solution of an alkali salt may be used as a mixture aqueous solution.

pH of the slurry for spray drying prepared as described above is preferably in the range from 1.5 to 5.5 and more preferably in the range from 3 to 5. When the pH is less than 1.5, pseudo boehmite alumina is dissolved excessively, so that such parameters as a specific surface area or a pore volume of the obtained catalytic composition become lower and the activity is apt to be deteriorated. When the pH is over 5.5, copper is precipitated as a hydroxide thereof at a high percentage before being spray-dried, so that the copper component can not homogeneously be deposited on an alumina carrier containing silica alumina particles, which may cause deterioration in the activity or in the longterm fluidity.

A concentration of the slurry for spray drying is preferably in the range from 5 to 25 wt % and more preferably in the range from 10 to 20 wt % when expressed as that of a solid content. When the concentration is less than 5 wt %, an average particle diameter of spherical microparticles obtained by spray drying becomes smaller, and a percentage of microparticles with the diameter of 20 µm or less becomes higher, and also the water content is high, which is not economical because thermal energy is required a lot. When the concentration is over 25 wt %, sometimes viscosity of the slurry is too high to be spray-dried.

It is to be noted that the slurry for spray drying may be subjected to emulsification, homogenization or the like with such as device as a homogenizer or a colloid mill according to the necessity.

Step (b)

The slurry for spray drying obtained in step (a) is spray-dried. There is not any specific restriction over a method for spray drying the slurry, so long as a micro-spherical fluidized catalyst can be obtained like with any known fluidized catalyst for oxychlorination, and for instance, various types of spray driers such as those based on the disk rotary system, the nozzle system, or the like may be used in a hot air flow.

In this step, a temperature of the hot air flow is preferably in the range from 150 to 500° C., and more preferably in the range from 200 to 350° C. When a temperature of the hot air flow is less than 150° C., and sometime the slurry is not dried sufficiently. On the other hand, when the temperature is over 500° C., the slurry is dried rapidly, which may cause polarization of the active components and promoters.

An average particle diameter of the spherical microparticles obtained by spray drying is preferably in the range from 50 to 80 µm and more preferably in the range from 55 from 75 µm. When the average particle diameter is less than 50 µm, sometimes an average particle diameter of catalytic particle obtained by calcining in the calcination step described later may be less than 40 µm, and in that case the sufficient fluidity can not be obtained, or loss of the catalytic particles may increase. When the average particle diameter is over 80 µm, an average particle diameter of the catalytic particles obtained by calcining in the calcination step described later may be over 75 µm, and the sufficient fluidity may not be obtained like in the case where the average particle diameter is too small.

In addition, diameter distribution of the spherical microparticles is preferably homogeneous, and a percentage of microparticles with the diameter of less than 30 µm is preferably 10 wt % or less, and a percentage of particles with the diameter of more than 90 µm is preferably 20 wt % or less. The preferable diameters can be classified more minutely, if required.

The average particle diameter and the particle diameter distribution can be obtained, for instance, by the micromesh sieve method.

Step (c)

The spherical microparticles obtained by spray drying are then subjected to a calcination process to obtain a catalytic composition for oxychlorination.

A temperature for calcination is preferably in the range from 350 to 850° C., and more preferably in the range from 500 to 700° C. When the temperature is less than 350° C., dehydration and crystallization of pseudo boehmite alumina (conversion to $\gamma$-$Al_2O_3$) are insufficient, and the activity and the selectivity of the catalytic composition for oxychlorination become insufficient presumably because bonding between the composition and the active components or promoters is insufficient. When the temperature for calcination is over 850° C., a crystal type of $\epsilon$-$Al_2O_3$ may change to that of $\epsilon$-$Al_2O_3$ or $\alpha$-$Al_2O_3$, or copper as an active component is completely oxidized, which makes the activity of the catalytic composition insufficient.

The time spent for calcination may be changed according to a temperature for calcination, and there is no specific restriction over the time, but generally the time is in the range from 0.1 to 24 hours.

The catalytic composition for oxychlorination according to the present invention is obtained as described above.

The catalytic composition for oxychlorination obtained as described above preferably contains copper by the content in the range from 5 to 20 wt % when expressed as that of an oxide thereof (CuO), an alkali earth metal by the content in the range from 0.1 to 6 wt % when expressed as that of an oxide thereof, an alkali metal by the content in the range from 0.1 to 3 wt % when expressed as an oxide thereof, a rare earth metal by the content in the range from 0.1 to 6 wt % when expressed as an oxide thereof, silica alumina particles by the content in the range from 5 to 40 wt %, and alumina as a carrier by the content in the range from 40 to 90 wt %, more preferably in the range from 60 to 82 wt %.

[Method of Manufacturing the Catalytic Composition for Oxychlorination (2)]

A method (2) of manufacturing the catalytic composition for oxychlorination according to the present invention comprises the following steps (a) to (f):

(a) a step of mixing an aqueous solution of an alkali metal aluminate, a dispersion liquid of silica alumina particles, and an aqueous solution of cupric salt in an aqueous solution of an aluminum salt;

(b) a step of preparing a slurry for spray drying by cleaning the mixture slurry;

(c) a step of spray drying the slurry;

(d) a step of cleaning the spray dried slurry;

(e) a step of drying the slurry; and (f) a step of calcining the slurry.

Step (a)

Such materials as aluminum chloride, aluminum nitrate, aluminum sulfate, and aluminum acetate may be used as an aluminum salt in the present invention.

Of these materials, when aluminum chloride is used, it is easy to prepare a fibrous pseudo boehmite alumina gel described in the manufacturing method (1) above, and it is possible to obtain a catalytic composition for oxychlorination having the excellent activity and selectivity.

A concentration of an aqueous solution of the aluminum salt as described above is preferably in the range from 0.1 to 5 wt % and more preferably in the range from 0.5 to 2 wt % when expressed as that of $Al_2O_3$. When the concentration of the aqueous solution of aluminum salt is less than 0.1 wt %, primary particles of the pseudo boehmite alumina are apt to become larger, and sometimes the specific surface area does not become higher with the activity deteriorated, and also the attrition resistance may be insufficient. When the concentration of the aqueous solution of aluminum salt is over 5 wt %, the primary particles of the pseudo boehmite alumina aggregate to form smaller particles, and sometimes the attrition resistance may be insufficient. Also the crystallinity is not improved and the activity is insufficient.

The alkali aluminate ($MAlO_2$: M representing an alkali metal) includes, but not limited to sodium aluminate, and potassium aluminate. When the sodium aluminate is used in combination with the aluminum chloride, it is easy to prepare the fibrous pseudo boehmite alumina gel, and it is possible to obtain a catalytic composition for oxychlorination excellent in activity and selectivity.

A concentration of the aqueous solution of alkali aluminate described above is preferably in the range from 0.1 to 30 wt %, and more preferably in the range from 1 to 25 wt % when expressed as that of $Al_2O_3$. When the concentration is less than 0.1 wt %, stability of the alkali metal aluminate is low when dissolved and alkali metal aluminate is easily hydrolyzed, which makes it difficult to prepare the fibrous pseudo boehmite alumina gel. When the concentration is over 30 wt %, primary particles of pseudo boehmite alumina aggregate to form smaller particles, and therefore sometimes the attrition resistance is insufficient and the crystallinity does not become higher with the activity deteriorated.

As the silica alumina particles, the silica alumina particles as described above are used.

A quantity of the silica alumina particles used in the process is adjusted so that a content of the silica alumina particles in an obtained catalytic composition is in the range from 5 to 40 wt % and more preferably in the range from 10 to 25 wt %.

There is no specific restriction over a concentration of a dispersion liquid of the silica alumina particles, and the concentration is generally in the range from 5 to 30 wt % as expressed as that of an oxide thereof.

The cupric salt, which may be used in the present invention, includes, but not limited to cupric chloride, cupric nitrate, copper sulfate, and cupric acetate. Of these materials, cupric chloride is preferable for obtaining a catalytic composition for oxychlorination excellent in activity and selectivity, presumably because cupric chloride associates a proper amount of chloride in the catalytic composition.

A concentration of an aqueous solution of the cupric salt can freely be adjusted according to a content of copper in the catalytic composition or the like, and generally the concentration is preferably in the range from 0.1 to 20 wt % and more preferably in the range from 1 to 5 wt %.

In this step, at first an aqueous solution of an alkali metal aluminate and an aqueous solution of cupric salt are mixed in an aqueous solution of an aluminum salt.

By mixing the aqueous solution of an alkali metal aluminate and the aqueous solution of cupric salt in the aqueous solution of an aluminum salt, it is possible to obtain a catalytic composition for oxychlorination which has a high specific surface area and also has high activity and high selectivity with the activity and selectivity little deteriorated even when used for a long time.

In this step, preferably the aqueous solution of an alkali metal aluminate is at first mixed in the aqueous solution of an aluminum salt, and then the dispersion liquid of silica alumina particles is added, and then the aqueous solution of a cupric salt is mixed in the mixture solution. If required, after the aqueous solutions are added, the mixture solution may be aged.

When the mixing method other than that described above is employed, namely for instance (1) when the aqueous solution of an aluminum salt, the aqueous solution of an alkali metal aluminate, the dispersion liquid of silica alumina particles, and the aqueous solution of a cupric salt are mixed together at prespecified ratios respectively, or (2) when the aqueous solution of an aluminum salt and the aqueous solution of a cupric salt are mixed together in the aqueous solution of an alkali metal aluminate, the improved attrition resistance and the improved hydrothermal resistance, which are the effects provided by the present invention, can not be attained, and also such properties as the activity, the selectivity, and the fluidity may sometimes be insufficient.

A ratio of a mole number of the aluminum salt (Ma) and a mole number of the alkali metal aluminate (Mb) (Ma/Mb) is preferably in the range from 0.1 to 0.45, and more preferably in the range from 0.15 to 0.35. When the molar ratio (Ma/Mb) is in the above-described range, it is easy to prepare a pseudo boehmite alumina gel comprising the fibrous primary and secondary particles, and it is possible to obtain a catalytic composition for oxychlorination having which is excellent in activity and selectivity and also in which the activity and the selectivity are deteriorated little and are preserved for a long time.

When the aqueous solution of an alkali metal aluminate is mixed in the aqueous solution of an aluminum salt, pH is preferably in the range from 7 to 12.5 and more preferably in the range from 8 to 12. When the pH is less than 7, sometimes the pseudo boehmite alumina gel comprising the fibrous primary and secondary particles can not be obtained, and when the pH is over 12, copper hydroxide (hydrate) generated by hydrolysis of the cupric salt aqueous solution subsequently mixed therein are not precipitated homogeneously on the pseudo boehmite alumina particles, and are sometimes precipitated in the separated state, and in this case, the activity, the selectivity, and the life as a catalyst are not sufficient.

Then the aqueous solution of cupric nitrate is added.

The aqueous solution of cupric nitrate is preferably mixed so that a content of CuO in the finally obtained catalytic composition is in the range described above.

There is no specific restriction over a temperature during the mixing step, and the temperature is generally in the range from 0 to 60° C., and more preferably at the range from 20 to 30° C. When the temperature at the mixing step is less than 0° C., sometimes a long time is required for precipitation of the copper component by hydrolysis of the cupric salt, or a content of the cupric component in the finally obtained catalyst may be insufficient. When the temperature at the mixing step is over 60° C., sometimes the activity, the selectivity, and the life as a catalyst may be insufficient, although the reason has not fully be clarified.

pH of the mixture slurry, when the aqueous solution of a cupric salt is mixed, is generally in the range from 4.0 to 9.5, and preferably in the range from 4.5 to 6.5. When the pH is not in the range above, because the fibrous pseudo boehmite particles can not be obtained, the attrition resistance is deteriorated, a specific surface area and a pore volume of the catalytic composition become smaller, and sometimes the activity, the selectivity, and the life as a catalyst may be insufficient.

In step (a), the mixture slurry may be aged according to the necessity. A temperature for aging is preferably in the range from 30 to 60° C., and more preferably in the range from 50 to 60° C.

By aging the mixture slurry under the conditions as described above, it is possible to manufacture, with high reproducibility, a catalytic composition for oxychlorination which is excellent in such properties as attrition resistance, activity, selectivity and generates organic halogenated compounds or the like as byproducts little.

In this step, like in the manufacturing method (1), it is preferable to mix at least one aqueous solution of metal salt selected from an aqueous solution of an alkali earth metal salt, an aqueous solution of a rare earth metal salt, and an aqueous solution of an alkali metal salt.

The aqueous solution of a metal salt as described above is preferably mixed in the aqueous solution of an aluminum salt previously, or together with or in succession to the aqueous solution of a cupric salt.

In step (a), an acid or an alkali may be mixed in so that pH of the mixture slurry is adjusted to and preserved in the range described above. Hydrochloric acid, nitric acid, or sulfuric acid or the like may be used as an acid, and an alkali metal hydroxide, ammonia, organic amine or the like may be used as an alkali.

Step (b)

The mixture slurry is cleaned to prepare a slurry for spray drying.

At first, the mixture slurry prepared in step (a) is subjected to filtering. Hot water or the like may be used at the filtering step, if required, and by subjecting the mixture slurry to filtering, excessive salts such as sodium chloride, and sodium nitrate can be reduced. By reducing the excessive salts, it is possible to obtain a catalytic composition excellent in such properties as attrition resistance.

Then the mixture slurry is subjected to filtering for dehydration or water is added for adjusting the concentration to prepare a slurry for spray drying, if required.

A concentration of the slurry for spray drying is preferably in the range from 5 to 20 wt % and more preferably in the range from 8 to 18 wt % when expressed as that of a solid content. When the concentration is less than 5 wt %, an average particle diameter of spherical particles obtained by spray-drying the slurry is apt to become smaller, while a percentage of microparticles with the diameter of 20 μm or less is apt to increase, and in addition a water content is high and thermal energy is required a lot for spray drying, which is not advantageous from the economical point of view. On the other hand, when the concentration is over 20 wt %, viscosity of the slurry is too high, and sometimes it is difficult to spray-dry the slurry.

The slurry for spray drying may be subjected to an emulsifying or homogenizing process, for instance, with a homogenizer or a colloid mill, if required.

pH of the slurry for spray-drying described above is in the range from 4 to 9.5, and more preferably in the range from 4.5 to 6.5. When the pH is less than 4, a specific surface area and a pore volume of the obtained catalyst are apt to become lower, and the activity and the life as a catalyst may become insufficient. When the pH is over 9.5, the activity, the life as a catalyst, and the long-term fluidity are apt to become lower, presumably because the copper components are not homogeneously precipitated on the alumina carrier.

Step (c)

The slurry for spray drying obtained in step (b) is spray-dried. The operation for spray-drying the slurry is performed like in the manufacturing method (1).

Step (d)

Then the microparticles obtained by spray-drying the slurry are cleaned. There is no specific restriction over the method of cleaning the microparticles, so long as impure salts other than effective components in the catalyst (alumina as a carrier component, silica alumina particles, copper as an active component, a rare earth metal, an alkali earth metal, and alkali metal as promoters) can be reduced or removed, and any known method may be employed.

For instance, the microparticles may be cleaned by dispersing the spherical microparticles obtained by spray-drying the slurry in water, filtering the sol, and pouring water (hot water) or the like over the filtrate. A content of residual salts as a solid content after cleaning is preferably 5 wt % or below, more preferably 2 wt % or below, and most preferably 1 wt % or below.

Step (e)

Then the cleaned spherical microparticles are dried. There is no specific restriction over the method of drying the microparticles, and any known method may be employed. There is not specific restriction over the temperature for drying the microparticles, but the temperature is generally in the range from 60 to 200° C., and more preferably in the range from 80 to 150° C. The time for drying is generally in the range from 1 to 24 hours, although the time varies according to the temperature employed for drying.

Step (f)

After the drying step, the microparticles are subjected to calcination to obtain the catalytic composition for oxychlorination. The calcination step is performed like in the manufacturing method (1).

[Method of Manufacturing a Catalytic Composition for Oxychlorination (3)]

A method (3) of manufacturing a catalytic composition for oxychlorination according to the present invention comprises the following steps (a) to (d):

(a) a step of adding carboxylic acid and/or hydroxycarboxylic acid in a pseudo boehmite alumina slurry and aging the mixture;

(b) a step of furthermore adding an acid and an aqueous solution of cupric nitrate in the mixture to prepare a slurry for spray drying;

(c) a step of spray drying the slurry; and (d) a step of calcining the microparticles obtained in step (c).

Step (a)

As a source for alumina, the pseudo boehmite alumina used in step (a) in the manufacturing method (1) is used.

When an average length ($L_1$) of the primary particles is less than 1 nm, dissolution of alumina proceeds excessively, and a pore volume and a specific surface area of the finally obtained catalyst become smaller and the activity is insufficient. When the average length ($L_1$) of the primary particles is over 10 nm, bulk density of the obtained catalyst decreases and the attrition resistance is insufficient.

When an average width ($W_1$) of the primary particles is less than 0.5 nm, dissolution of alumina proceeds excessively, and a pore volume and a specific surface area of the finally obtained catalyst become smaller and the activity is insufficient like in the case where the average length ($L_1$) is less than 1 nm.

When the average width ($W_1$) of the primary particles is over 3 nm, the bulk density of the obtained catalyst is low and the attrition resistance is insufficient.

In the method (3), after the cleaning step, carboxylic acid and/or hydroxycarboxylic acid are added in the pseudo boehmite slurry, and the mixture solution is aged.

The carboxylic acid used in this step includes, but not limited to monocarboxylic acids such as formic acid, acetic acid, oxalic acid, acrylic acid (unsaturated carboxylic acid), and gluconic acid, and multivalent carboxylic acids such as malic acid, oxalic acid, malonic acid, succinic acid, glutaric acid, adipic acid, sebacic acid, maleic acid, fumaric acid, and phthalic acid.

The hydroxycarboxylic acid (having a carboxyl group and a hydroxyl group in one molecule) used in this step includes, but not limited to α-lactic acid, β-lactic acid, γ-hydroxy valeric acid, glyceric acid, tartaric acid, citric acid, tropic acid, and benzilic acid. The carboxylic acid and/or the hydroxycarboxylic acid are preferably added in the form of an aqueous solution.

A molar ratio of a mole number ($M_C$) of the carboxylic acid and/or hydroxycarboxylic acid and a mole number ($M_A$) of the pseudo boehmite alumina slurry when expressed as that of $Al_2O_3$ ($M_C/M_A$) is preferably in the range from 0.005 to 0.1, and more preferably in the range from 0.010 to 0.05.

When the molar ratio ($M_C/M_A$) is less than 0.005, the effect of the carboxylic acid and/or the hydroxycarboxylic acid is weak, and sometimes the effect of improving a specific surface area of the catalyst can not be obtained, and also the effect of improving the activity and the selectivity of the catalyst can not be obtained sufficiently.

When the molar ratio ($M_C/M_A$) is over 0.1, although the initial activity of the catalyst is high, the activity is quickly deteriorated, and also the selectivity is apt to drop, so that the cost performance becomes lower.

In the manufacturing method (3), there is no specific restriction over a concentration of the pseudo boehmite alumina slurry so long as the slurry can be aged statically or with agitation after the carboxylic acid and/or the hyctroxycarboxylic acid are added therein. The concentration is generally in the range from 2 to 20 wt % and preferably in the range from 5 to 18 wt % when expressed as that of $Al_2O_3$, because readjustment of the slurry to be spray-dried is not required when the concentration is in the range described above.

When the concentration of the pseudo boehmite alumina slurry is less than 2 wt % as that of $Al_2O_3$, the concentration of the slurry for spray drying becomes lower and a percentage of the obtained spherical microparticles increases. In this case, the fluidity lowers and the catalyst can not be captured with a cyclone, so that the catalyst loss disadvantageously increases.

When a concentration of the pseudo boehmite alumina slurry as that of $Al_2O_3$ is over 20 wt %, sometimes the concentration of the slurry for spray drying is too high and also the viscosity is high. In this case, spray drying may be difficult, and even if spray drying can be carried out, dispersibility of the active components is insufficient, so that performance of the obtained catalyst may be insufficient and also such properties as attrition resistance or bulk specific density (CBD) may become lower.

Aging is performed statically or with agitation in the range from 50 to 100° C., and preferably in the range from 60 to 95° C. Agitation may be performed only when the temperature is raised or dropped.

When the temperature for aging is less than 50° C., the reaction between the carboxylic acid and/or the hydroxycarboxylic acid and the pseudo boehmite is not performed sufficiently. In this case, sometimes the effect for improving a specific surface area of the catalyst can not be obtained, and also the effect for improving activity and selectivity of the catalyst may not be obtained. When the temperature for aging is over 100° C., sometimes crystallization of the pseudo boehmite occurs and a specific surface area of the catalyst becomes smaller. In this case, the effect for improving activity and selectivity may not be obtained.

Step (b)

An acid is added to the pseudo boehmite alumina slurry obtained in step (a) of the manufacturing method (1).

Then an aqueous solution of a cupric nitrate is added like in step (a) of the manufacturing method (1).

Preferably at least one of an aqueous solution of an alkali earth metal salt, an aqueous solution of a rare earth metal salt, and an aqueous solution of an alkali metal salt is added together with or after the aqueous solution of cupric nitrate is added.

Like in the manufacturing method (1), a concentration of the slurry for spray drying is preferably in the range from 5 to 25 wt % and more preferably in the range from 10 to 20 wt % when expressed as that of the solid content.

Step (c)

Then the slurry for spray drying obtained in step (b) is spray-dried like in the manufacturing method (1).

Step (d)

The spherical microparticles obtained by spray-drying the slurry is calcined like in the manufacturing method (1) to obtain a catalytic composition for oxychlorination.

EXAMPLES

The present invention is described with reference to examples thereof, but the present invention is not limited to the examples.

Example 1

[Catalytic Composition for Oxychiorination (1)]

Preparation of a Slurry for Spray Drying (1)

10.8 Kg of an aqueous solution of sodium aluminate with the concentration of 5 wt % when expressed as that of $Al_2O_3$ and 10.8 Kg of an aqueous solution of aluminum sulfate with the concentration of 2.5 wt % when expressed as that of $Al_2O_3$ were mixed with each other to prepare an alumina hydrogel slurry. In this step, the temperature for preparing the alumina hydrogel slurry was 60° C. and the pH was 9.5.

Then the alumina hydrogel slurry was filtered and the filtrate was cleaned with pure water at the temperature of 60° C. to obtain 5.40 Kg of pseudo boehmite alumina slurry with the concentration of 15 wt % when expressed as that of $Al_2O_3$.

A portion of the pseudo boehmite alumina slurry was dried, and observed with a scan electronic microscope to find that the slurry comprised fibrous secondary particles in which fibrous primary particles with the average length of 3 nm and the average width of 1 nm aggregated to form bundles.

Separately, 430 g of a silica sol (produced by Catalysts & Chemicals Industries Co., Ltd.: SI-40 with the average particle diameter of 17 nm and the concentration of 40 wt %) was mixed in 3.0 Kg of pure water, and 15.1 g of a cationic metal hydrate compound (produced by Taki Chemical CO., Ltd.: PAC #1000, $Al_2O_3$=23.34 wt %, Cl=8.06 wt %, and basicity=83.44%) was mixed in the mixture solution above, and the resultant solution was agitated for 12 hours to prepare 3.45 Kg of a dispersion liquid of silica alumina particles (1) based on silica particles coated with alumina with the $SiO_2.Al_2O_3$ concentration of 5.1 wt %. An average particle diameter of the silica alumina particles (1) and a content of $Al_2O_3$ are shown in Table 1.

100 g of nitric acid with the concentration of 63 wt % was mixed in the dispersion liquid above, and furthermore 367.3 g of a cupric nitrate trihydrate ($Cu(NO_3)_2.3H_2O$) with the concentration (purity) of 97 wt %, 48.3 g of lanthanum nitrate hexahydrate with the concentration of 99 wt % (La$(NO_3)_3 \cdot 6H_2O$), 47.5 g of cerium nitrate hexahydrate with the concentration of 98 wt % ($Ce(NO_3)_3 \cdot 6H_2O$), and 228.5 g of magnesium nitrate hexahydrate with the concentration of 98 wt % ($Mg(NO_3)_2 \cdot 6H_2O$) were dissolved in the mixture dispersion liquid above to prepare an aqueous solution of mixed nitrates with the concentration of 8.54 wt % when expressed as that of [$SiO_2 \cdot Al_2O_3 + CuO + La_2O_3 + Ce_2O_3 + MgO$].

After the temperature of the cleaned pseudo boehmite alumina slurry was adjusted to 50° C., and then the aqueous solution of mixed nitrates was mixed in the slurry.

Then, the mixture slurry was homogenized with a homogenizer to prepare the slurry (1) for spray drying. pH of the slurry was 3.6.

Spray Drying

The slurry for spray drying (1) was sprayed in a hot air flow at the temperature of 220° C. to obtain spherical microparticles (1). An average particle diameter of the spherical microparticles (1) was 65 μm, and a percentage of the microparticles with the diameter of 20 μm or below was 10 wt %, while those with the diameter of 149 μm or more was 5 wt %.

Calcination

The spherical microparticles (1) were calcined in a rotary calcination furnace for 0.5 hours at 650° C. to prepare a catalytic composition for oxychlorination (1).

[Measurement and Assessment of the Physical Properties]

A CBD, an average particle diameter, attrition resistance, a specific surface area (SA), composition, and a crystal type of alumina of the catalytic composition for oxychlorination (1) are as shown in Table 1.

The attrition resistance was measured by the method described in JP 737,429 C, and is shown in Table 1 by a wt % of microparticles recovered by flowing the composition under the conditions of a quantity of filled catalyst of 50 g, the nozzle diameter of 0.406 mmφ, and the air flow rate of 0.425 $m^3$/hour, and also by recovering the microparticles scattered from a fluid bed vessel for a period of time from 5 hours in start of flowing until 20 hours in start of flowing.

The physical properties of the catalytic compositions obtained in the following examples and comparative examples were also measured and assessed as described above.

[Assessment of the Catalytic Performance]

The catalytic performance of the catalytic composition for oxychlorination (1) was assessed as described below, and a result of the assessment is shown in Table 1. The catalytic performance was assessed likely also for the catalytic compositions obtained in examples and comparative examples described below.

(1) Assessment of Activity 5 g of the catalytic composition for oxychlorination (1) was filled in a fixed fluid bed reactor, and was fluidized at the temperature of 230° C. by supplying a nitrogen gas at the rate of 28.8 ml/min, and then a mixture gas for reaction (ethylene by 39.2 vol %, hydrochloric acid by 46.1 vol %, and oxygen by 14.7 vol %) was supplied at the range of 62.5 ml/min. The WHSV in this step was 750 (L/Hr./Kg Cat.).

The generated gas was analyzed by means of the gas chromatography, and the activity, the selectivity, the yield, and the combustibility were as shown in Table 1.

Activity: Conversion ratio to hydrochloric acid=(Supplied hydrochloric acid−hydrochloric acid not reacted yet)/Supplied hydrochloric acid×100 (mole %)

Selectivity: Selectivity for EDC=Net amount of produced EDC/Theoretical amount of EDC to be produced×100 (mole %)

Yield (in case of hydrochloric acid): Yield of EDC=Conversion ratio to hydrochloric acid× Selectivity for EDC (mole %)

Combustibility: Combustion rate of ethylene=(CO+ $CO_2$) mole number/$C_2H_2$ mole number×100 (mole %)

(2) Assessment of Fluidity

A different between a temperature at a lower section of a fluid bet and a temperature at an upper section of the fluid bet (ΔT: ° C.) was measured during the reaction, and the difference was assessed on the following criteria.

ΔT of less than 3° C. and good fluidity shown: ◉

ΔT of 3° C. or more and less than 5° C. and relatively good fluidity shown: ○

ΔT of 5° C. or more and less than 7° C. and acceptable fluidity shown: Δ

ΔT of 7° C. or more and not-acceptable fluidity shown: X (3) Accelerated Deterioration Test (3-1) Assessment Based on Activity Drop Percentage The test for activity above was performed for 50 hours continuously to measure a conversion ratio to hydrochloric acid, and a decreasing rate was obtained by comparing the measured conversion ratio to the initial ratio. The assessment was made on the following criteria.

Decreasing rate in conversion ratio to hydrochloric acid of less than 10%: ◉

Decreasing rate in conversion ratio to hydrochloric acid in the range from 10% to less than 20%: ○

Decreasing rate in conversion ratio to hydrochloric acid in the range from 20% to less than 30%: Δ

Decreasing rate in conversion ratio to hydrochloric acid of 30% or more: X (3-2) Assessment Based on a Decreasing Rate of a Specific Surface Area After the reaction was completed, the catalyst was taken out, and the decreasing rate was obtained by comparing a specific surface area of the catalyst calcined for 0.5 hours at 400° C. to that of the catalytic composition for oxychlorination (1), and the assessment was made on the following criteria.

Decreasing rate of the specific surface area of less than 10%: ◉

Decreasing rate of the specific surface area in the range from 10% to less than 20%: ○

Decreasing rate of the specific surface area in the range from 20% to less than 30%: Δ

Decreasing rate of the specific surface area of more 30% or more: X

Example 2

[Catalytic Composition for Oxychlorination (2)]

A slurry for spray drying (2) was prepared like in Example 1 excluding the point that 2.29 Kg of a dispersion liquid of silica alumina particles (1) with the $SiO_2 \cdot Al_2O_3$ concentration of 5.1 wt % was used. pH of the slurry was 3.8.

Then the slurry was spray-dried like in Example 1, and was calcined to prepare the catalytic composition for oxychlorination (2). An average particle diameter of the spherical microparticles (2) spray-dried as described above was 65 μm.

A percentage of the microparticles with the diameter of 20 μm or below was 10 wt %, and a percentage of the microparticles with the diameter of 149 μm or more was 5 wt %.

Example 3

[Catalytic Composition for Oxychlorination (3)]

A slurry for spray drying (3) was prepared like in Example 1 excluding the point that 4.61 Kg of a dispersion liquid of silica alumina particles (1) with the $SiO_2.Al_2O_3$ concentration of 5.1 wt % was used. pH of the slurry was 3.7.

Then the slurry was spray-dried like in Example 1, and was calcined to prepare the catalytic composition for oxychlorination (3). An average particle diameter of the spherical microparticles (3) spray-dried as described above was 65 μm. A percentage of the microparticles with the diameter of 20 μm or below was 10 wt %, and a percentage of the microparticles with the diameter of 149 μm or more was 5 wt %.

Example 4

[Catalytic Composition for Oxychlorination (4)]

Like in Example 1, 438 g of a silica sol (produced by Catalysts & Chemicals Industries Co., Ltd.: SI-40 with the average particle diameter of 17 nm and the concentration of 40 wt %) was mixed in 3.0 Kg of pure water, and 3.8 g of a cationic metal hydrate compound (produced by Taki Chemical CO., Ltd.: PAC #1000, $Al_2O_3$=23.34 wt %, Cl=8.06 wt %, and basicity=83.44%), and 11.3 g of pure water were mixed in the mixture solution above, and the resultant solution was agitated for 12 hours to prepare 3.45 Kg of a dispersion liquid of silica alumina particles (4) based on silica particles coated with alumina with the $SiO_2.Al_2O_3$ concentration of 5.1 wt %. An average particle diameter of the silica alumina particles (4) and a content of $Al_2O_3$ are shown in Table 1.

Then the catalytic composition for oxychlorination (4) was prepared like in Example 1 excluding the point that a dispersion liquid of the silica alumina particles (4) were used. An average particle diameter of the spherical microparticles (4) spray-dried as described above was 65 μm. A percentage of the microparticles with the diameter of 20 μm or below was 10 wt %, and a percentage of the microparticles with the diameter of 149 μm or more was 5 wt %.

Example 5

[Catalytic Composition for Oxychlorination (5)]

Like in Example 1, 418 g of a silica sol (produced by Catalysts & Chemicals Industries Co., Ltd.: SI-40 with the average particle diameter of 17 nm and the concentration of 40 wt %) was mixed in 3.0 Kg of pure water, and 37.7 g of a cationic metal hydrate compound (produced by Taki Chemical CO., Ltd.: PAC #1000, $Al_2O_3$=23.34 wt %, Cl=8.06 wt %, and basicity=83.44%) and 11.3 g of pure water were mixed in the mixture solution above, and the resultant solution was agitated for 12 hours to prepare 3.45 Kg of a dispersion liquid of silica alumina particles (5) based on silica particles coated with alumina with the $SiO_2.Al_2O_3$ concentration of 5.1 wt %. An average particle diameter of the silica alumina particles (5) and a content of $Al_2O_3$ are shown in Table 1.

Then the catalytic composition for oxychlorination (5) was prepared like in Example 1 excluding the point that a dispersion liquid of the silica alumina particles (5) were used. An average particle diameter of the spherical microparticles (5) spray-dried as described above was 65 μm. A percentage of the microparticles with the diameter of 20 μm or below was 10 wt %, and a percentage of the microparticles with the diameter of 149 μm or more was 5 wt %.

Example 6

[Catalytic composition for Oxychlorination (6)]

Like in Example 1, 860 g of a silica sol (produced by Catalysts & Chemicals Industries Co., Ltd.: SI-550 with the average particle diameter of 5 nm and the concentration of 20 wt %) was mixed in 2.66 Kg of pure water, and 15.1 g of a cationic metal hydrate compound (produced by Taki Chemical CO., Ltd.: PAC #1000, $Al_2O_3$=23.34 wt %, Cl=8.06 wt %, and basicity=83.44%) was mixed in the mixture solution above, and the resultant solution was agitated for 12 hours to prepare 3.45 Kg of a dispersion liquid of silica alumina particles (6) based on silica particles coated with alumina with the $SiO_2.Al_2O_3$ concentration of 5.1 wt %. An average particle diameter of the silica alumina particles (6) and a content of $Al_2O_3$ are shown in Table 1.

Then the catalytic composition for oxychlorination (6) was prepared like in Example 1 excluding the point that a dispersion liquid of the silica alumina particles (6) were used. An average particle diameter of the spherical microparticles (6) spray-dried as described above was 65 μm. A percentage of the microparticles with the diameter of 20 μm or below was 10 wt %, and a percentage of the microparticles with the diameter of 149 μm or more was 5 wt %.

Example 7

[Catalytic Composition for Oxychlorination (7)]

Like in Example 1, 366 g of a silica sol (produced by Catalysts & Chemicals Industries Co., Ltd.: SI-50 with the average particle diameter of 26 nm and the concentration of 47 wt %) was mixed in 3.064 Kg of pure water, and 15.1 g of a cationic metal hydrate compound (produced by Taki Chemical CO., Ltd.: PAC #1000, $Al_2O_3$=23.34 wt %, Cl=8.06 wt %, and basicity=83.44%) was mixed in the mixture solution above, and the resultant solution was agitated for 12 hours to prepare 3.45 Kg of a dispersion liquid of silica alumina particles (7) based on silica particles coated with alumina with the $SiO_2.Al_2O_3$ concentration of 5.1 wt %. An average particle diameter of the silica alumina particles (7) and a content of $Al_2O_3$ are shown in Table 1.

Then the catalytic composition for oxychlorination (7) was prepared like in Example 1 excluding the point that a dispersion liquid of the silica alumina particles (7) were used. An average particle diameter of the spherical microparticles (7) spray-dried as described above was 65 μm. A percentage of the microparticles with the diameter of 20 μm or below was 10 wt %, and a percentage of the microparticles with the diameter of 149 μm or more was 5 wt %.

Example 8

[Catalytic Composition for Oxychlorination (8)]

3.45 Kg of a dispersion liquid of silica alumina particles (8) based on silica particles coated with alumina with the $SiO_2.Al_2O_3$ concentration of 5.1 wt % was prepared like in Example 1 excluding the point that, as a cationic metal hydrate compound (aluminum compound), 24.1 g of aluminum sulfate 18-hydrate (produced by Kanto Chemical Co., Ltd. with the $Al_2O_3$ concentration of 14.6 wt %) was used. An average diameter of the silica alumina particles (8) and a content of $Al_2O_3$ are as shown in Table 1.

Then, the catalytic composition for oxychlorination (8) was prepared like in Example 1 excluding the point that the silica alumina particles (8) were used. An average particle diameter of the spherical microparticles (8) spray-dried as described above was 65 μm. A percentage of the microparticles with the diameter of 20 μm or below was 10 wt %, and a percentage of the microparticles with the diameter of 149 μm or more was 5 wt %.

Example 9

[Catalytic Composition for Oxychlorination (9)]

A slurry for spray drying (9) was prepared like in Example 1 excluding the point that 24.6 g of potassium nitrate with the purity of 98 wt % was used in place of 219.6 g of magnesium nitrate hexahydrate with the purity of 98 wt %. pH of the slurry was 3.7.

Then the catalytic composition for oxychlorination (9) were prepared by spray-drying and calcining the slurry like in Example 1. An average particle diameter of the spherical microparticles (9) spray-dried as described above was 65 μm. A percentage of the microparticles with the diameter of 20 μm or below was 10 wt %, and a percentage of the microparticles with the diameter of 149 μm or more was 5 wt %.

Example 10

[Catalytic Composition for Oxychlorination (10)]

Preparation of a Slurry for Spray Drying (10)

1.22 Kg of aluminum chloride hexahydrate with the purity of 99 wt % (containing $Al_2O_3$ by 22.07%) was dissolved in 4.18 Kg of pure water, and then 3.72 Kg of the dispersion liquid (1) of silica alumina particles based on silica particles coated with alumina with the $SiO_2.Al_2O_3$ concentration of 5.1 wt % prepared like in Example 1 was added in the solution above to prepare an aqueous solution of aluminum chloride.

10.8 Kg of an aqueous solution of sodium aluminate with the concentration of 5 wt % when expressed as that $Al_2O_3$ was added to prepare an alumina hydrogel slurry. A temperature at the mixing step was 30° C. and pH of the alumina hydrogel slurry was 11.5.

Then the alumina hydrogel slurry was subjected to filtering, and the filtrate was cleaned with pure water at the temperature of 60° C. to obtain 6.66 Kg of alumina slurry with the concentration of 15 wt % when expressed as that of $Al_2O_3$.

A portion of the alumina hydrogel slurry was dried and observed with scan electron microscope to find the fibrous secondary particles in which fibrous primary particles with the average length of 10 nm and the average width of 0.5 nm were formed into bundles. Also X-ray diffraction was performed to find that the alumina hydrogel was pseudo boehmite alumina.

Separately, 534 g of cupric chloride dehydrate with the purity of 97 wt % (containing CuO by 45.2 wt %), 156.1 g of an aqueous solution of a rough rare earth metal chloride with the concentration of 30 wt %, and 242.6 g of magnesium chloride hexahydrate with the purity of 98 wt % (containing MgO by 19.3 wt %) were dissolved in 8.116 Kg of pure water to prepare 8.86 Kg of an aqueous solution of mixture salts with the concentration of 3 wt % when expressed as that of $[CuO+RE_2O_3+MgO]$.

The aqueous solution of mixture salts was mixed in the alumina hydrogel slurry to prepare a mixture hydrogel slurry. pH of the mixture hydrogel slurry was 6.1.

Then, the mixture hydrogel slurry was dehydrated and also demineralized, and then pure water as added to adjust the solid content to 10 wt %. The mixture slurry was then homogenized with a homogenizer to prepare a slurry for spray drying (10). pH of the slurry for spray drying (10) was 6.8.

Spray Drying

The slurry for spray drying (10) was sprayed into a hot air flow at the temperature of 250° C. to obtain spherical microparticles (10). An average particle diameter of the spherical microparticles (10) was 65 μm. A percentage of the microparticles with the diameter of 20 μm or below was 10 wt %, and a percentage of the microparticles with the diameter of 149 μm or more was 5 wt %.

Cleaning

The spherical microparticles (10) were suspended in hot water at 60° C. with the amount 10 times larger in weight as compared to that of the particles, and the suspension liquid was filly agitated and filtered, and the filtrate was cleaned with hot water at 60° C. with the 10-times larger amount.

Calcination

The filtrate was dried for 2 hours at 120° C. and was then calcined for 0.5 hours at 400° C. in a rotary calcination furnace to prepare a catalytic composition for oxychlorination (10).

Example 11

[Catalytic Composition for Oxychlorination (11)]

Preparation of a Slurry for Spray Drying (11)

A slurry for spray drying (11) was prepared like in Example 10 excluding the point that a dispersion liquid of the silica alumina particles (8) based on silica particles coated with alumina with the $SiO_2.Al_2O_3$ concentration of 5.1 wt % prepared like in Example 8 was used. pH of the slurry for spray drying (11) was 6.8.

Then the slurry was spray-dried and calcined like in Example 10 to prepare a catalytic composition for oxychlorination (11). An average particle diameter of the spherical microparticles (11) was 65 μm. A percentage of the microparticles with the diameter of 20 μm or below was 10 wt %, and a percentage of the microparticles with the diameter of 149 μm or more was 5 wt %.

Comparative Example 1

[Catalytic Composition for Oxychlorination (R1)]

A slurry for spray drying (R1) was prepared like in Example 1 excluding the point that a dispersion liquid of silica alumina particles (1) was not used. pH of the slurry was 3.7.

Then the slurry was spray-dried and calcined like in Example 1 to prepare a catalytic composition for oxychlorination ($R_1$). An average particle diameter of the spherical microparticles (R1) was 65 μm. A percentage of the microparticles with the diameter of 20 μm or below was 10 wt %, and a percentage of the microparticles with the diameter of 149 μm or more was 5 wt %.

Comparative Example 2

[Catalytic Composition for Oxychlorination (R2)]

A slurry for spray drying (R2) was prepared like in Example 1 excluding the point that 440 g of a silica sol (produced by Catalysts & Chemicals Industries Co., Ltd.: SI-40 with the average particle diameter of 17 nm and the concentration of 40 wt %) was used in place of the dispersion liquid of the silica alumina particles (1). pH of the slurry was 3.7.

Then the slurry was spray-dried and calcined like in Example 1 to prepare a catalytic composition for oxychlorination (R2). An average particle diameter of the spherical microparticles (R2) was 65 μm. A percentage of the microparticles with the diameter of 20 μm or below was 10 wt %, and a percentage of the microparticles with the diameter of 149 μm or more was 5 wt %.

Comparative Example 3

[Catalytic Composition for Oxychlorination (R3)]

A catalytic composition for oxychlorination (R3) was prepared like in Example 10 excluding the point that the dispersion liquid of silica alumina particles (1) was not used. pH of the slurry was 3.7.

Then the slurry was spray-dried and calcined like in Example 10 to prepare a catalytic composition for oxychlorination (R3). An average particle diameter of the spray-dried spherical microparticles (R3) was 65 μm. A percentage of the microparticles with the diameter of 20 μm or below was 10 wt %, and a percentage of the microparticles with the diameter of 149 μm or more was 5 wt %.

Comparative Example 4

[Catalytic Composition for Oxychlorination (R4)]

A slurry for spray drying (R4) was prepared like in Example 10 excluding the point that 440 g of a silica sol (produced by Catalysts & Chemicals Industries Co., Ltd.: SI-40 with the average particle diameter of 17 nm and the concentration of 40 wt %) was used in place of the dispersion liquid of the silica alumina particles (1). pH of the slurry was 3.7.

Then the slurry was spray-dried and calcined like in Example 1 to prepare a catalytic composition for oxychlorination (R4). An average particle diameter of the spray-dried spherical microparticles (R4) was 65 μm. A percentage of the microparticles with the diameter of 20 μm or below was 10 wt %, and a percentage of the microparticles with the diameter of 149 μm or more was 5 wt %.

TABLE 1

| | | Properties of catalyst | | | | Catalyst composition | | | | | | |
|---|---|---|---|---|---|---|---|---|---|---|---|---|
| | | | | | | | Silica alumina particles | | | | | |
| | Manufacturing Method | CBD ml/g | Av. Particle diameter μm | Attrition resistance wt %/15 hr | SA m²/g | Av. Diameter of silica particles (nm) | SiO₂ content (wt %) | Al₂O₃ content (wt %) | Average diameter of silica alumina particles (nm) | wt % in catalyst | Copper oxide wt % | Alkali earth metal oxide wt % | La₂O₃ wt % |
| Example 1 | (1) | 1.03 | 65 | 0.6 | 196 | 17 | 98.0 | 2.0 | 18 | 15.0 | 10.0 | 3.0 | 1.5 |
| Example 2 | (1) | 1.03 | 65 | 0.5 | 203 | 17 | 98.0 | 2.0 | 18 | 10.0 | 10.7 | 3.2 | 1.6 |
| Example 3 | (1) | 1.01 | 65 | 0.8 | 185 | 17 | 98.0 | 2.0 | 18 | 20.0 | 9.4 | 2.8 | 1.4 |
| Example 4 | (1) | 1.03 | 65 | 0.7 | 196 | 17 | 99.5 | 0.5 | 17 | 15.0 | 10.0 | 3.0 | 1.5 |
| Example 5 | (1) | 1.03 | 65 | 0.6 | 208 | 17 | 95.0 | 5.0 | 19 | 15.0 | 10.0 | 3.0 | 1.5 |
| Example 6 | (1) | 1.04 | 65 | 0.6 | 214 | 5 | 98.0 | 2.0 | 6 | 15.0 | 10.0 | 3.0 | 1.5 |
| Example 7 | (1) | 1.03 | 65 | 0.9 | 185 | 26 | 98.0 | 2.0 | 26 | 15.0 | 10.0 | 3.0 | 1.5 |
| Example 8 | (1) | 1.04 | 65 | 0.7 | 195 | 17 | 98.0 | 2.0 | 18 | 15.0 | 10.0 | 3.0 | 1.5 |
| Example 9 | (1) | 1.03 | 65 | 0.7 | 195 | 17 | 98.0 | 2.0 | 18 | 15.1 | 10.2 | — | 1.5 |
| Example 10 | (2) | 1.02 | 65 | 1.8 | 253 | 17 | 98.0 | 2.0 | 18 | 15.0 | 15.0 | 3.0 | — |
| Example 11 | (2) | 1.02 | 65 | 1.8 | 248 | 17 | 98.0 | 2.0 | 18 | 28.7 | 9.9 | 2.1 | — |
| Comp. Ex. 1 | (1) | 1.05 | 65 | 0.5 | 210 | — | — | — | — | — | 11.8 | 3.5 | 1.76 |
| Comp. Ex. 2 | (1) | 1.02 | 65 | 0.9 | 205 | 17 | 100 | — | — | 15.0 | 10.0 | 3.0 | 1.5 |
| Comp. Ex. 3 | (2) | 1.03 | 65 | 1.7 | 270 | — | — | — | — | — | 17.6 | 3.5 | — |
| Comp. Ex. 4 | (2) | 1.02 | 65 | 2.2 | 350 | 17 | 100 | — | — | 15.0 | 10.0 | 3.0 | 1.5 |

| | Catalyst composition | | | | | Catalytic performance | | | | | |
|---|---|---|---|---|---|---|---|---|---|---|---|
| | Ce₂O₃ wt % | RE₂O₃ wt % | Alkali metal oxide wt % | Alumina Type | Alumina wt % | Conversion rate of HCl mol % | Selectivity for EDC mol % | Ethylene combustion rate mol % | Yield of EDC mol % | Fluidity | Accelerated deterioration test (1) (2) |
| Example 1 | 1.5 | — | — | γ | 69.0 | 98.7 | 98.8 | 2.0 | 95.6 | ⊚ | ⊚ ⊚ |
| Example 2 | 1.6 | — | — | γ | 73.0 | 98.5 | 98.9 | 2.0 | 95.5 | ⊚ | ⊚ ⊚ |
| Example 3 | 1.4 | — | — | γ | 65.0 | 98.9 | 98.8 | 1.9 | 95.9 | ◯ | ⊚ ⊚ |
| Example 4 | 1.5 | — | — | γ | 69.0 | 98.9 | 98.9 | 2.2 | 95.7 | ⊚ | ⊚ ⊚ |
| Example 5 | 1.5 | — | — | γ | 69.0 | 98.8 | 98.8 | 1.9 | 95.8 | ⊚ | ◯ ◯ |
| Example 6 | 1.5 | — | — | γ | 69.0 | 98.6 | 98.7 | 2.0 | 95.3 | ⊚ | ⊚ ⊚ |
| Example 7 | 1.5 | — | — | γ | 69.0 | 98.8 | 98.8 | 2.1 | 95.6 | ⊚ | ⊚ ◯ |
| Example 8 | 1.5 | — | — | γ | 69.0 | 98.9 | 98.8 | 1.9 | 95.9 | ⊚ | ⊚ ⊚ |
| Example 9 | 1.5 | — | 1.0 | γ | 70.6 | 98.3 | 98.9 | 1.7 | 95.8 | ⊚ | ⊚ ⊚ |
| Example 10 | — | 3.0 | — | γ | 64.0 | 98.8 | 98.7 | 2.4 | 95.1 | ⊚ | ⊚ ⊚ |
| Example 11 | — | 3.0 | — | γ | 64.0 | 98.8 | 98.9 | 2.3 | 95.5 | ◯ | ⊚ ⊚ |
| Comp. Ex. 1 | 1.76 | — | — | γ | 81.1 | 98.5 | 98.3 | 2.6 | 94.3 | ⊚ | ◯ Δ |
| Comp. Ex. 2 | 1.5 | — | — | γ | 69.0 | 98.3 | 98.5 | 2.7 | 94.2 | ◯ | ◯ ⊚ |

TABLE 1-continued

| | | | | | | | | | | | | |
|---|---|---|---|---|---|---|---|---|---|---|---|---|
| Comp. Ex. 3 | — | 3.5 | — | γ | 75.3 | 99.0 | 98.9 | 3.4 | 94.6 | ◎ | ○ | Δ |
| Comp. Ex. 4 | 1.5 | — | — | γ | 69.0 | 98.8 | 98.7 | 3.1 | 94.5 | ○ | ○ | ◎ |

Example 21

[Preparation of a Catalytic Composition for Oxychlorination (21)]

Preparation of a Slurry for Spray Drying (21)

74.7 Kg of an aqueous solution of sodium aliiminate with the concentration of 5 wt % when expressed as that of $Al_2O_3$ and 74.7 Kg of an aqueous solution of aluminum sulfate with the concentration of 2.5 wt % when expressed as that of $Al_2O_3$ were mixed to prepare an alumina hydrogel slurry. The temperature employed for preparation of the alumina hydrogel slurry was 60° C. and the pH was 9.5.

Then, the alumina hydrogel slurry was subjected to filtering, and the filtrate was cleaned with pure water at 60° C. to obtain 5.60 Kg of pseudo boehmite alumina slurry with the concentration of 15 wt % when expressed as that of $Al_2O_3$.

Then, an aqueous solution prepared by dissolving 0.05 Kg of gluconic acid in 0.35 Kg of pure water was added to the alumina hydrogel slurry, and the resultant mixture was aged for 5 hours at 80° C. A portion of the pseudo boehmite alumina slurry was dried, and was observed with a scan electronic microscope. The obtained particles were fibrous secondary particles based on fibrous primary particles with the average length of 2.8 nm and the average width of 1 nm formed into bundles.

0.31 Kg of cupric nitrate trihydrate with the concentration of 97 wt % ($Cu(NO_3)_2.3H_2O$), 0.04 Kg of lanthanum nitrate hexahydrate ($La((NO_3)_3.6H_2O$) with the concentration of 99 wt %, 0.04 Kg of cerium nitrate hexahydrate ($Ce(NO_3)_3.6H_2O$) with the concentration of 98 wt %, and 0.20 Kg of magnesium nitrate hexahydrate ($Mg(NO_3)_2.6H_2O$) with the concentration of 98 wt % were dissolved in diluted nitric acid prepared by adding 0.1 Kg of nitric acid with the concentration of 63 wt % in 0.45 Kg of pure water to prepare 1.14 Kg of an aqueous solution of mixture nitrates with the concentration of 14 wt % when expressed as that of $[CuO+La_2O_3+Ce_2O_3+MgO]$.

After a temperature of the cleaned pseudo boehmite alumina slurry was adjusted to 50° C., and the aqueous solution of mixture nitrate was mixed therein.

The mixture slurry was homogenized with a homogenizer to prepare 7.14 Kg of a slurry (21) for spray drying. pH of the slurry was 3.5.

Spray Drying

The slurry (21) of spray drying was sprayed into a hot air flow at the temperature of 220° C. to obtain spherical microparticles (21).

An average particle diameter of the spherical microparticles (21) was 65 μm. A percentage of the microparticles with the diameter of 20 μm or below was 10 wt %, and a percentage of the microparticles with the diameter of 149 μm or more was 5 wt %.

Calcination

Then the spherical microparticles (21) were calcined for 0.5 hours at 650° C. to prepare a catalytic composition for oxychlorination (21).

An average particle diameter, a CBD, a crystal type of alumina, and a composition of the catalytic composition for oxychlorination (21) are shown together the compositions obtained in the examples and comparative examples described below in Table 2.

Example 22

[Preparation of a Slurry for Spray Drying (22)]

7.14 Kg of a slurry for spray drying (22) was prepared like in Example 21 excluding the point that 0.02 Kg of gluconic acid and 0.38 Kg of pure water were added in the alumina hydrosol in place of 0.05 Kg of gluconic acid and 0.35 Kg of pure water. pH of the slurry was 3.5.

Spray Drying

The slurry of spray drying (22) was sprayed into a hot air flow at the temperature of 220° C. to obtain spherical microparticles (22).

An average particle diameter of the spherical microparticles (22) was 65 μm. A percentage of the microparticles with the diameter of 20 μm or below was 10 wt %, and a percentage of the microparticles with the diameter of 149 μm or more was 5 wt %.

Calcination

Then the spherical microparticles (22) were calcined for 0.5 hours in a rotary calcination furnace at 650° C. to prepare a catalytic composition for oxychlorination (22).

Example 23

[Preparation of a Catalytic Composition for Oxychlorination (23)]

Preparation of a Slurry for Spray Drying (23)

7.14 Kg of a slurry for spray drying (23) was prepared like in Example 21 excluding the point that 0.08 Kg of gluconic acid and 0.32 Kg of pure water were added in the alumina hydrosol in place of 0.05 Kg of gluconic acid and 0.35 Kg of pure water. pH of the slurry was 3.3.

Spray Drying

The slurry of spray drying (23) was sprayed into a hot air flow at the temperature of 220° C. to obtain spherical microparticles (23).

An average particle diameter of the spherical microparticles (23) was 65 μm. A percentage of the microparticles with the diameter of 20 μm or below was 10 wt %, and a percentage of the microparticles with the diameter of 149 μm or more was 5 wt %.

Calcination

Then the spherical microparticles (23) were calcined for 0.5 hours in a rotary calcination furnace at 650° C. to prepare a catalytic composition for oxychlorination (23).

Example 24

[Preparation of a Slurry for Spray Drying (24)]

7.14 Kg of a slurry for spray drying (23) was prepared like in Example 21 excluding the point that 0.05 Kg of gluconic acid to be added in the alumina hydrosol was changed to 0.05 Kg of citric acid with the concentration of 99.5%. pH of the slurry was 3.5.

Spray Drying

The slurry of spray drying (24) was sprayed into a hot air flow at the temperature of 220° C. to obtain spherical microparticles (24).

An average particle diameter of the spherical microparticles (24) was 65 µm. A percentage of the microparticles with the diameter of 20 µm or below was 10 wt %, and a percentage of the microparticles with the diameter of 149 µm or more was 5 wt %.

Calcination

Then the spherical microparticles (24) were calcined for 0.5 hours in a rotary calcination furnace at 650° C. to prepare a catalytic composition for oxychlorination (24).

Example 25

[Preparation of a Slurry for Spray Drying (25)]

7.14 Kg of a slurry for spray drying (25) was prepared like in Example 21 excluding the point that 0.31 Kg of pure water and 0.15 Kg of a rare earth metal chloride of $RECl_3$ with the concentration of 30 wt % were used in place of 0.45 Kg of pure water, 0.04 Kg of lanthanum nitrate with the concentration of 99 wt %, and 0.04 Kg of cerium nitrate hexahydrate with the concentration of 98 wt %. pH of the slurry was 3.5.

Spray Drying

The slurry (25) of spray drying was sprayed into a hot air flow at the temperature of 220° C. to obtain spherical microparticles (25).

An average particle diameter of the spherical microparticles (25) was 65 µm. A percentage of the microparticles with the diameter of 20 µm or below was 10 wt %, and a percentage of the microparticles with the diameter of 149 µm or more was 5 wt %.

Calcination

Then the spherical microparticles (25) were calcined for 0.5 hours in a rotary calcination furnace at 650° C. to prepare a catalytic composition for oxychlorination (25).

Example 26

[Preparation of a Slurry for Spray Drying (26)]

7.14 Kg of a slurry for spray drying (26) was prepared like in Example 21 excluding the point that 0.36 Kg of pure water, 0.15 Kg of a rare earth metal chloride with the concentration of 30 wt %, and 0.15 Kg of magnesium chloride with the concentration of 98% were used in place of 0.45 Kg of pure water, 0.04 Kg of lanthanum nitrate hexahydrate with the concentration of 99 wt %, 0.4 Kg of cerium nitrate hexahydrate with the concentration of 98 wt %, and 0.20 Kg of magnesium nitrate hexahydrate with the concentration of 98 wt %. pH of the slurry was 3.3.

Spray Drying

The slurry (26) of spray drying was sprayed into a hot air flow at the temperature of 220° C. to obtain spherical microparticles (26).

An average particle diameter of the spherical microparticles (26) was 65 µm. A percentage of the microparticles with the diameter of 20 µm or below was 10 wt %, and a percentage of the microparticles with the diameter of 149 µm or more was 5 wt %.

Calcination

Then the spherical microparticles (26) were calcined for 0.5 hours in a rotary calcination furnace at 650° C. to prepare a catalytic composition for oxychlorination (26).

Example 27

[Preparation of a Catalytic Composition for Oxychlorination (27)]

Preparation of a Slurry for Spray Drying (27)

7.14 Kg of a slurry for spray drying (27) was prepared like in Example 21 excluding that 0.56 kg of pure water and 0.02 Kg of potassium carbonate ($K_2CO_3$) with the concentration of 99 wt % were used in place of 0.45 Kg of pure water and 0.20 Kg of magnesium nitrate hexahydrate with the concentration of 98%. pH of the slurry was 3.7.

Spray Drying

The slurry of spray drying (27) was sprayed into a hot air flow at the temperature of 220° C. to obtain spherical microparticles (27).

An average particle diameter of the spherical microparticles (27) was 65 µm. A percentage of the microparticles with the diameter of 20 µm or below was 10 wt %, and a percentage of the microparticles with the diameter of 149 µm or more was 5 wt %.

Calcination

Then the spherical microparticles (27) were calcined for 0.5 hours in a rotary calcination furnace at 650° C. to prepare a catalytic composition for oxychlorination (27).

Comparative Example 21

[Preparation of a Catalytic Composition for Oxychiorination (R21)]

Preparation of a Slurry for Spray Drying (R21)

74.7 Kg of an aqueous solution of sodium aluminate with the concentration of 5 wt % when expressed as that of $Al_2O_3$ and 74.7 Kg of an aqueous solution of aluminum sulfate with the concentration of 2.5 wt % as converted to that of $Al_2O_3$ were mixed with each other to prepare an alumina hydrogel slurry. A temperature employed in the mixing step was 60° C. and pH was 9.5.

The alumina hydrogel slurry was subjected to filtering, and the filtrate was cleaned with pure water at 60° C. to obtain 5.60 Kg of pseudo boehmite alumina slurry with the concentration of 15 wt % when expressed as that of $Al_2O_3$.

A portion of the pseudo boehmite alumina slurry was dried and observed with a scan electron microscope to find that the particles were fibrous secondary particles in which fibrous primary particles with the average length of 3 nm and the average width of 1 nm were formed into bundles.

Separately, 0.27 Kg of a cupric chloride dihydrate with the concentration of 98 wt %, 0.18 Kg of an aqueous solution of a rare earth metal chloride with the concentration of 30 wt %, and 0.16 Kg of a magnesium chloride hexahydrate with the concentration of 98% were dissolved in a distilled hydrochloric acid prepared by adding 0.11 Kg of hydrochloric acid with the concentration of 35 wt % in 1.24 Kg of pure water to prepare 1.96 Kg of an aqueous solution of mixture hydrochloride with the concentration of 15 wt % when expressed as that of $[CuO+La_2O_3+Ce_2O_3+MgO]$.

A temperature of the cleaned pseudo boehmite alumina slurry was adjusted to 50° C., and the aqueous solution of mixture hydrochloride was mixed in the slurry.

The mixture slurry was homogenized with a homogenizer to prepare 7.56 Kg of a slurry for spray drying (R21). pH of the slurry was 3.2.

Spray Drying

The slurry for spray drying (R21) was sprayed into a hot air flow at the temperature of 220° C. to obtain spherical microparticles (R21).

An average particle diameter of the spherical microparticles (R21) was 65 μm. A percentage of the microparticles with the diameter of 20 μm or below was 10 wt %, and a percentage of the microparticles with the diameter of 149 μm or more was 5 wt %.

Calcination

Then the spherical microparticles (R21) were calcined for 0.5 hours in a rotary calcination furnace at 650° C. to prepare a catalytic composition for oxychlorination (R21).

Comparative Example 22

[Preparation of a Catalytic Composition for Oxychlorination (R22)]

Preparation of a Slurry for Spray Drying (R22)

7.56 Kg of a slurry for spray drying (R22) was prepared like in Comparative Example 21 excluding the point that 1.42 Kg of pure water and 0.02 Kg of potassium chloride (KCl) with the concentration of 97 wt % were used in place of 1.24 Kg of pure water and 0.20 Kg of magnesium nitrate hexahydrate with the concentration of 98%. pH of the slurry was 3.4.

Spray Drying

The slurry for spray drying (R22) was sprayed into a hot air flow at the temperature of 220° C. to obtain spherical microparticles (R22).

An average particle diameter of the spherical microparticles (R22) was 65 μm. A percentage of the microparticles with the diameter of 20 μm or below was 10 wt %, and a percentage of the microparticles with the diameter of 149 μm or more was 5 wt %.

Calcination

Then the spherical microparticles (R22) were calcined for 0.5 hours in a rotary calcination furnace at 650° C. to prepare a catalytic composition for oxychlorination (R22).

Comparative Example 23

[Preparation of a Catalytic Composition for Oxychiorination (R23)]

Preparation of a Slurry for Spray Drying (R23)

74.7 Kg of an aqueous solution of sodium aluminate with the concentration of 5 wt % when expressed as that of $Al_2O_3$ and 74.7 Kg of an aqueous solution of aluminum sulfate with the concentration of 2.5 wt % as converted to that of $Al_2O_3$ were mixed with each other to prepare an alumina hydrogel slurry. A temperature employed in the mixing step was 60° C. and pH was 9.5.

The alumina hydrogel slurry was subjected to filtering, and the filtrate was cleaned with pure water at 60° C. to obtain 5.60 Kg of pseudo boehmite alumina slurry with the 15 wt % when expressed as that of $Al_2O_3$.

A portion of the pseudo boehmite alumina slurry was dried and observed with a scan electron microscope to find that the particles were fibrous secondary particles in which fibrous primary particles with the average length of 3 nm and the average width of 1 nm were formed into bundles.

Separately, 0.31 Kg of cupric nitrate trihydrate ($Cu(NO_3)_2 \cdot 3H_2O$) with the concentration of 97 wt %, 0.04 Kg of lanthanum nitrate hexahydrate ($La(NO_3)_3 \cdot 6H_2O$) with the concentration of 99 wt %, 0.04 Kg of cerium nitrate hexahydrate ($Ce(NO_3)_2 \cdot 6H_2O$) with the concentration of 98 wt %, and 0.20 Kg of magnesium nitrate hexahydrate ($Mg(NO_3)_2 \cdot 6H_2O$) were dissolved in distilled nitric acid prepared by adding 0.10 Kg of nitric acid with the concentration of 63 wt % in 0.38 Kg of pure water to prepare 1.07 Kg of an aqueous solution of mixture nitrate with the concentration of 15 wt % when expressed as that of $[CuO+La_2O_3+Ce_2O_3+MgO]$.

A temperature of the cleaned pseudo boehmite alumina slurry was adjusted to 50° C., and then the aqueous solution of mixture nitrate was mixed in the slurry.

Then the mixture slurry was homogenized with a homogenizer to prepare 6.67 Kg of a slurry for spray drying (R23). pH of the slurry was 3.5.

Spray Drying

The slurry for spray drying (R23) was sprayed into a hot air flow at the temperature of 220° C. to obtain spherical microparticles (R23).

An average particle diameter of the spherical microparticles (R23) was 65 μm. A percentage of the microparticles with the diameter of 20 μm or below was 10 wt %, and a percentage of the microparticles with the diameter of 149 μm or more was 5 wt %.

Calcination

Then the spherical microparticles (R23) were calcined for 0.5 hours in a rotary calcination furnace at 650° C. to prepare a catalytic composition for oxychlorination (R23).

TABLE 2

| | Preparation of slurry | | | Slurry for spray drying | | | | | | | Catalyst | |
| | | | | Pseudo behmite slurry | | | | Conc. | | | | Av. |
| | Conc. of | Carboxylic acid | | Primary particles | | | | of solid | Conc. of | | | particle |
| | $Al_2O_3$ wt % | Type | Molar ratio of carboxylic acid/$Al_2O_3$ | Length nm | Width nm | Conc. wt % | pH | content wt % | halogens wt % | Corrosiveness | CBD ml/g | diameter μm |
|---|---|---|---|---|---|---|---|---|---|---|---|---|
| Example 21 | 14 | Gluconic acid | 0.031 | 2.8 | 1 | 14 | 3.5 | 14 | — | ⊙ | 1.05 | 65 |
| Example 22 | 14 | Gluconic acid | 0.012 | 2.9 | 1 | 14 | 3.5 | 14 | — | ⊙ | 1.05 | 65 |
| Example 23 | 14 | Gluconic acid | 0.050 | 2.5 | 0.9 | 14 | 3.4 | 14 | — | ⊙ | 1.05 | 65 |
| Example 24 | 14 | Citric acid | 0.031 | 2.9 | 1 | 14 | 3.5 | 14 | — | ⊙ | 1.06 | 65 |
| Example 25 | 14 | Gluconic acid | 0.031 | 2.8 | 1 | 14 | 3.5 | 14 | — | ⊙ | 1.07 | 65 |

TABLE 2-continued

| | | | | | | | | | | | | |
|---|---|---|---|---|---|---|---|---|---|---|---|---|
| Example 26 | 14 | Gluconic acid | 0.031 | 2.8 | 1 | 14 | 3.3 | 14 | — | ◎ | 1.10 | 65 |
| Example 27 | 14 | Gluconic acid | 0.031 | 2.8 | 1 | 14 | 3.7 | 14 | — | ◎ | 1.03 | 65 |
| Comp. Ex. 21 | 15 | — | — | 3 | 1 | 15 | 3.2 | 15 | 7.6 | X | 1.25 | 65 |
| Comp. Ex. 22 | 15 | — | — | 3 | 1 | 1.5 | 3.4 | 1.5 | 7.0 | X | 1.20 | 65 |
| Comp. Ex. 23 | 15 | — | — | 3 | 1 | 15 | 3.5 | 15 | — | ◎ | 1.05 | 65 |

| | Catalyst | | | | | | | | | | | |
|---|---|---|---|---|---|---|---|---|---|---|---|---|
| | Catalyst composition | | | | | | | Catalytic performance | | | | |
| | | | Alkali | | | | | | | | | |
| | Attrition resistance | Copper oxide | earth metal oxide | Rare earth metal oxide | | Alkali metal oxide | Alumina | | Conversion rate of HCl | Selectivity for EDC | Ethylene combustion rate | Yield of EDC | |
| | wt %/ 15 hr | wt % | wt % | La2O3 wt % | Ce2O3 wt % | wt % | Type | wt % | mol % | mol % | mol % | mol % | Fluidity |
| Example 21 | 0.5 | 10.0 | 3.0 | 1.5 | 1.5 | — | γ | 84.0 | 99.8 | 99.8 | 2.2 | 97.4 | ◎ |
| Example 22 | 0.5 | 10.0 | 3.0 | 1.5 | 1.5 | — | γ | 84.0 | 99.7 | 99.8 | 2.2 | 97.3 | ◎ |
| Example 23 | 0.6 | 10.0 | 3.0 | 1.5 | 1.5 | — | γ | 84.0 | 99.8 | 99.8 | 2.4 | 97.2 | ◎ |
| Example 24 | 0.5 | 10.0 | 3.0 | 1.5 | 1.5 | — | γ | 84.0 | 99.8 | 99.8 | 2.2 | 97.4 | ◎ |
| Example 25 | 0.5 | 10.0 | 3.0 | 1.5 | 1.5 | — | γ | 84.0 | 99.8 | 99.7 | 2.3 | 97.2 | ○ |
| Example 26 | 0.5 | 10.0 | 3.0 | 1.5 | 1.5 | — | γ | 84.0 | 99.7 | 99.7 | 2.3 | 97.1 | ○ |
| Example 27 | 0.5 | 10.0 | — | 1.5 | 1.5 | 1.0 | γ | 86.0 | 99.6 | 99.8 | 2.1 | 97.3 | ○ |
| Comp. Ex. 21 | 0.6 | 10.0 | 3.0 | 1.5 | 1.5 | — | γ | 84.0 | 98.7 | 99.2 | 2.5 | 95.5 | Δ |
| Comp. Ex. 22 | 0.9 | 10.0 | — | 1.5 | 1.5 | 1.0 | γ | 86.0 | 98.9 | 99.1 | 2.5 | 95.6 | Δ |
| Comp. Ex. 23 | 0.5 | 10.0 | 3.0 | 1.5 | 1.5 | — | γ | 84.0 | 98.8 | 99.3 | 2.4 | 95.8 | ◎ |

What is claimed is:

1. A catalytic composition for oxychlorination comprising:
silica alumina particles in an amount of 5 to 40 wt % as an oxide,
copper in an amount of 5 to 20 wt % as an oxide (CuO), and
a carrier alumina in an amount of 40 to 90 wt % as $Al_2O_3$,
wherein the silica alumina particles are included separately from the carrier alumina and comprise silica particles with alumina coatings.

2. The catalytic composition for oxychlorination according to claim 1, wherein an average particle diameter of the silica alumina particles is in a range from 3 to 100 nm, and a content of alumina in the silica alumina particles is in an amount from 0.1 to 10 wt %.

3. The catalytic composition for oxychlorination according to claim 1, further comprising an alkali earth metal in an amount from 0.1 to 6 wt % as MO, where M represents an alkali earth metal and O represents an oxide.

4. The catalytic composition for oxychlorination according to claim 3, wherein the alkali earth metal is magnesium.

5. The catalytic composition for oxychlorination according to claim 1, further comprising a rare earth metal in an amount from 0.1 to 6 wt % as $RE_2O_3$, where RE represents a rare earth metal and O represents an oxide.

6. The catalytic composition for oxychlorination according to claim 1, further comprising an alkali metal in an amount from 0.1 to 3 wt % as $N_2O$, where N represents an alkali metal and O representing an oxide.

7. The catalytic composition for oxychlorination according to claim 6, wherein the alkali metal is potassium.

8. The catalytic composition for oxychlorination according to claim 1, wherein the carrier alumina is γ-$Al_2O_3$.

9. A catalytic composition for oxychlorination comprising:
silica alumina particles in an amount of 5 to 40 wt %,
copper oxide in an amount of 5 to 20 wt %, and
$Al_2O_3$ as a carrier in an amount of 40 to 90 wt %,
wherein the silica alumina particles are included separately from the carrier and comprise silica particles with alumina coatings, and
wherein an average particle diameter of the silica alumina particles is in a range from 3 to 100 nm, and a content of alumina in the silica alumina particles is in an amount from 0.1 to 10 wt %.

* * * * *